US011634378B2

(12) United States Patent  
Arnatt et al.

(10) Patent No.: US 11,634,378 B2  
(45) Date of Patent: Apr. 25, 2023

(54) COMPOUNDS AND METHODS TARGETING GPER IN CALCIUM DISORDERS

(71) Applicant: Saint Louis University, St. Louis, MO (US)

(72) Inventors: Christopher Kent Arnatt, Kirkwood, MO (US); Chelsea DeLeon, Saint Louis, MO (US)

(73) Assignee: SAINT LOUIS UNIVERSITY, St. Louis, MO (US)

( * ) Notice: Subject to any disclaimer, the term of this patent is extended or adjusted under 35 U.S.C. 154(b) by 0 days.

(21) Appl. No.: 16/498,571

(22) PCT Filed: Mar. 29, 2018

(86) PCT No.: PCT/US2018/025117  
§ 371 (c)(1),  
(2) Date: Sep. 27, 2019

(87) PCT Pub. No.: WO2018/183659  
PCT Pub. Date: Oct. 4, 2018

(65) Prior Publication Data  
US 2021/0087134 A1 Mar. 25, 2021

Related U.S. Application Data

(60) Provisional application No. 62/478,947, filed on Mar. 30, 2017.

(51) Int. Cl.
| | |
|---|---|
| C07C 211/48 | (2006.01) |
| C07C 211/55 | (2006.01) |
| C07C 211/54 | (2006.01) |
| C07C 211/43 | (2006.01) |
| C07C 217/58 | (2006.01) |
| A61P 1/16 | (2006.01) |
| A61K 45/06 | (2006.01) |
| A61K 31/137 | (2006.01) |

(52) U.S. Cl.  
CPC ............. *C07C 211/48* (2013.01); *A61P 1/16* (2018.01); *C07C 217/58* (2013.01)

(58) Field of Classification Search  
CPC ... C07C 211/48; C07C 211/55; C07C 211/54; C07C 211/43; C07C 217/58; A61P 1/16; A61K 45/06; A61K 31/137  
See application file for complete search history.

(56) References Cited

U.S. PATENT DOCUMENTS 7,491,748 B2 * 2/2009 Tani .................... A61P 13/12  
560/21  
2008/0280938 A1 11/2008 Mori et al.

OTHER PUBLICATIONS

RN117-28-2, registry database compound, 1984.*  
RN861933-09-7, registry database compound, 2005.*  
RN1057106-35-0, registry database compound, 2008.*  
1984RN5260-71-9, registry database compound,.*  
RN499154-35-7, registry database compound, 2003.*  
Roque et al., Frontiers in Neuroendocrinology, 55, 2019, 100786 (13 pages).*  
Jacquot et al., Frontiers in Neuroendocrinology, 12, 2021, 794332 (2 pages).*  
Arnatt et al., "G Protein-Coupled Estrogen Receptor (GPER) Agonist Dual Binding Mode Analyses Toward Understanding of Its Activation Mechanism: A Comparative Homology Modeling Approach" *Molecular Informatics*, 32 (7), 647-658, 2013.  
Arnatt et al., "A Nuclear G Protein-coupled Estrogen Receptor, GPER. Homology Modeling Studies Toward Its Ligan-binding Mode Characterization," *Computational Approaches to Nuclear Receptors*, The Royal Society of Chemistry: pp. 117-137, 2012.  
Baell and Holloway, "New Substructure Filters for Removal of Pan Assay Interference Compounds (PAINS) From Screening Libraries and for Their Exclusion in Bioassays" *Journal of Medicinal Chemistry*, 53 (7), 2719-2740, 2010.  
Bissantz et al., "A Medicinal Chemist's Guide to Molecular Interactions" *Journal of Medicinal Chemistry*, 53 (14), 5061-5084, 2010.  
Bologa et al., "Virtual and Biomolecular Screening Converge on a Selective Agonist for GPR30" *Nature chemical biology*, 2 (4), 207-12, 2006.  
Chimento et al., "Oleuropein and Hydroxytyrosol Activate GPER/GPR30-dependent Pathways Leading to Apoptosis of ER-negative SKBR3 Breast Cancer Cells" *Molecular Nutrition & Food Research*, 58 (3), 478-489, 2014.  
Dennis et al., "Identification of a GPER/GPR30 Antagonist With Improved Estrogen Receptor Counterselectivity" *J Steroid Biochem Mol Biol*, 127 (3-5), 358-66, 2011.  
Dennis et al., "In Vivo Effects of a GPR30 Antagonist" *Nature chemical biology*, 5 (6), 421-7, 2009.  
Everhart J., "The burden of digestive diseases in the United States" *US Department of Health and Human Services, Public Health Service, National Institutes of Health, National Institute of Diabetes and Digestive and Kidney Diseases*, Ed. US Government Printing Office: Washington, DC, pp. NIH Publication No. 09-6443 pp. 115-117, 137-147, 2004.  
International Search Report for Application No. PCT/US18/025117, dated Jul. 20, 2018, 4 pgs.  
Kumar et al., "Overview of the Structural Basis for Transcription Regulation by Nuclear Hormone Receptors" *Essays In Biochemistry*, 40, 27, 2004.  
Lappano et al., "A Calixpyrrole Derivative Acts as an Antagonist to GPER, a G-protein Coupled Receptor: Mechanisms and Models" *Dis Model Mech*, 8 (10), 1237-46, 2015.  
Matthews & Gustafsson, "Estrogen Signaling: A Subtle Balance Between ER Alpha and ER Beta" *Mol Interv*, 3 (4), 281-92, 2003.  
Mendez-Luna et al., "Deciphering the GPER/GPR30-agonist and Antagonists Interactions Using Molecular Modeling Studies, Molecular Dynamics, and Docking Simulations" *Journal of biomolecular structure & dynamics*, 33 (10), 2161-72, 2015.

(Continued)

*Primary Examiner* — Sun Jae Yoo  
(74) *Attorney, Agent, or Firm* — Parker Highlander PLLC

(57) ABSTRACT

The present disclosure provides compositions and method targeting GPER for the treatment of cancers, such as breast cancers and leukemias, gallstone disease, and for conferring of neuroprotection on a subject. Also disclosed are high throughput assays for identifying antagonists of GPER.

20 Claims, 11 Drawing Sheets

(56) References Cited

OTHER PUBLICATIONS

Moreno-Ulloa et al., "The Effects of (-)-Epicatechin on Endothelial Cells Involve the G Protein-Coupled Estrogen Receptor (GPER)" *Pharmacological Research*, 100 (Supplement C), 309-320, 2015.
Pubchem, Substance Record for SID 274241496, Dec. 18, 2015, https://pubchem.ncbi.nlm.nih.gov/substance/274241496.
Pubchem, Substance Record for SID 252522752, Oct. 5, 2015, https://pubchem.ncbi.nlm.nih.gov/substance/252522752.
Rosano et al., Macromolecular Modelling and Docking Simulations for the Discovery of Selective GPER Ligands *Aaps j*, 18 (1), 41-6, 2016.
Vidad et al., "Locating the Ligand Binding Sites for the G—protein Coupled Estrogen Receptor (GPER) Using Combined Information from Docking and Sequence Conservation," *bioRxiv* 2016.

\* cited by examiner

Control   50 nM   30 nM   10 nM

| Antagonist | IC$_{50}$ (SKBR-3) | IC$_{50}$ (HL-60) |
|---|---|---|
| G-36 | ~20 nM | 1.35 μM ± 0.218 μM |
| G-15 | 20 nM | 0.967 μM ± 0.610 μM |

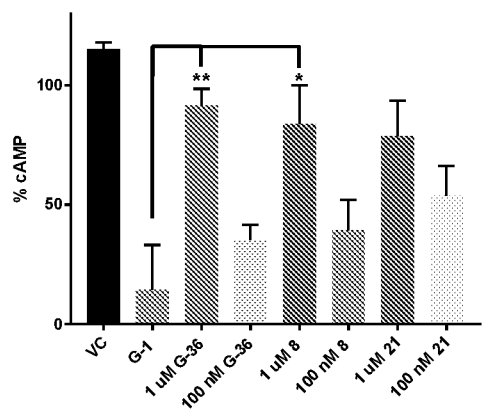
FIG. 13
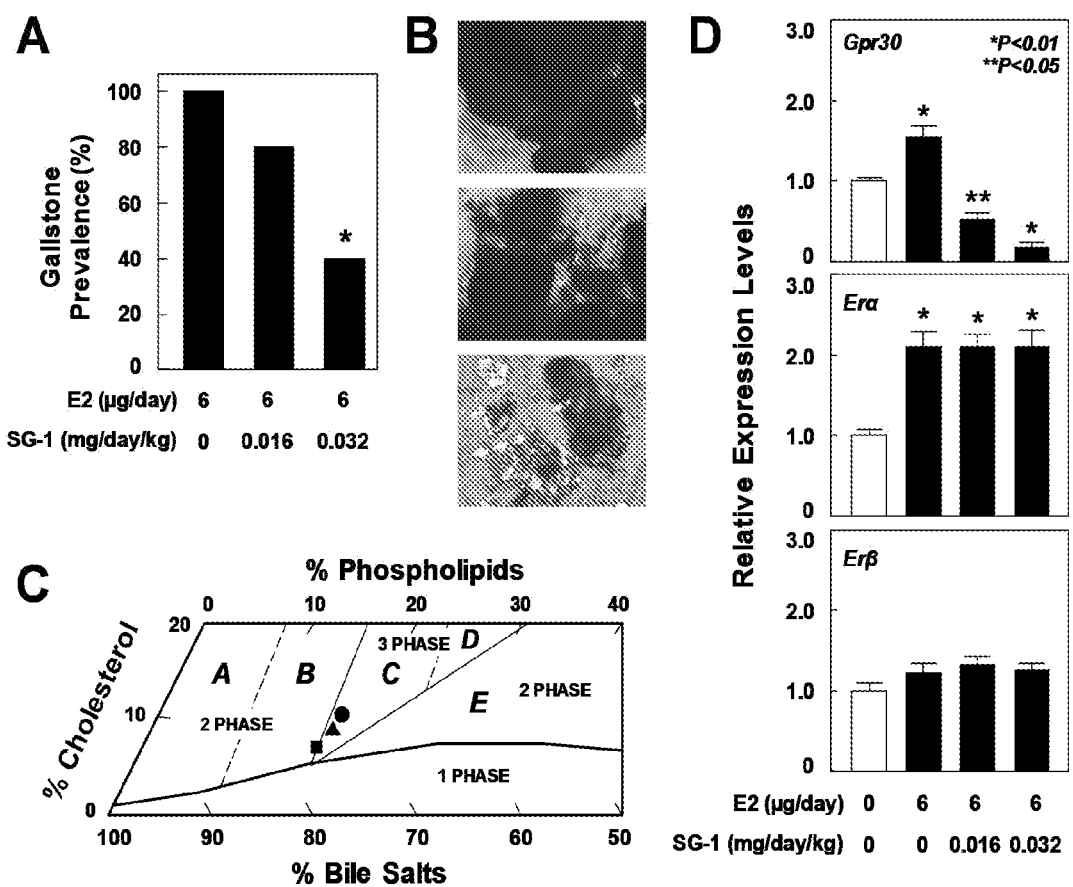
FIGS. 14A-D

COMPOUNDS AND METHODS TARGETING GPER IN CALCIUM DISORDERS

This application is a national phase application under 35 U.S.C. § 371 of International Application No. PCT/US2018/025117, filed Mar. 29, 2018, which claims benefit of priority to U.S. Provisional Application Ser. No. 62/478,947, filed Mar. 30, 2017, the entire contents of each of which are hereby incorporated by reference.

BACKGROUND

I. Field

The present disclosure relates generally to the fields of oncology, molecular biology, and medicine. More particularly, the disclosure relates to compositions and methods for treating diseases by targeting GPER, such as breast cancer, hormonal cancers, leukemia (acute and chronic), neuroprotection, and gallstone disease.

II. Description of Related Art

Breast cancer is a global health problem for which new and improved therapies continue to be needed. In the United States alone, there were 216,000 cases of invasive breast cancer and 40,000 deaths in 2004. Worldwide, breast cancer is the second most common type of cancer after lung cancer (10.4% of all cancer incidence, both sexes counted) and the fifth most common cause of cancer death. In 2004, breast cancer caused 519,000 deaths worldwide (7% of cancer deaths; almost 1% of all deaths). Breast cancer is about 1000 times more frequent among women than among men, although the number of male breast cancers is growing. Survival rates are equal in both sexes, but the prognosis for Stage 3 and 4 cancer patients (when initially diagnosed) is unfortunately not favorable.

Classical estrogen receptors (estrogen receptors α and β), have been shown to cause cell proliferation in a variety of breast cancers upon interaction with estrogenic compounds; however, G-protein estrogen receptor (GPER) has also been linked to cell proliferation, in the presence of estrogens in breast cancers absent Estrogen receptors α and β. However, this target remains unexploited, and the generation of new therapeutic modalities targeting GPER, as a monotherapy, or in combination with other established breast cancer therapies, would constitute a significant advance in care for breast cancer.

SUMMARY

Thus, in accordance with the present disclosure, there is provided a compound of the formula:

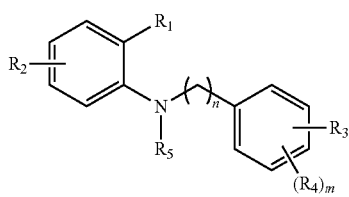

wherein:

$R_1$ is alkyl$_{(C\leq12)}$, cycloalkyl$_{(C\leq12)}$, aryl$_{(C\leq12)}$, or a substituted version of either of these two groups;

$R_2$ is alkyl$_{(C\leq12)}$, cycloalkyl$_{(C\leq12)}$, aryl$_{(C\leq12)}$, or a substituted version of any of these groups;

$R_3$ and $R_4$ are each independently hydrogen, amino, halo, or hydroxy, or alkyl$_{(C\leq12)}$, cycloalkyl$_{(C\leq12)}$, aryl$_{(C\leq12)}$, alkoxy$_{(C\leq12)}$, or a substituted version of any of these groups; or $R_3$ and $R_4$ are taken together and are alkenediyl$_{(C\leq8)}$ and form a second aromatic ring;

$R_5$ is hydrogen, alkyl$_{(C\leq6)}$, or substituted alkyl$_{(C\leq6)}$;

m is 0, 1, 2, or 3; and n is 0, 1, or 2;

or pharmaceutically acceptable salts thereof. The compound may be further defined as:

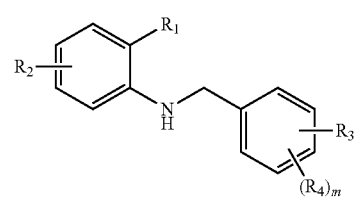

wherein:

$R_1$ is cycloalkyl$_{(C\leq12)}$, aryl$_{(C\leq12)}$, or a substituted version of either of these two groups;

$R_2$ is alkyl$_{(C\leq12)}$, cycloalkyl$_{(C\leq12)}$, aryl$_{(C\leq12)}$, or a substituted version of any of these groups;

$R_3$ and $R_4$ are each independently hydrogen, amino, halo, or hydroxy, or alkyl$_{(C\leq12)}$, cycloalkyl$_{(C\leq12)}$, aryl$_{(C\leq12)}$, alkoxy$_{(C\leq12)}$, or a substituted version of any of these groups; or $R_3$ and $R_4$ are taken together and are alkenediyl$_{(C\leq8)}$ and form a second aromatic ring; and m is 0, 1, 2, or 3;

or a pharmaceutically acceptable salt thereof. The compound may be further defined as:

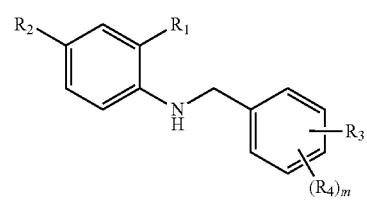

wherein $R_1$, $R_2$, $R_3$, $R_4$, and m are as defined above; or a pharmaceutically acceptable salt thereof.

In more particular embodiments, $R_1$ may be cycloalkyl$_{(C\leq8)}$ or substituted cycloalkyl$_{(C\leq8)}$, such as cyclopropyl, cyclopentyl, or cyclohexyl, $R_2$ may be alkyl$_{(C\leq6)}$ or substituted alkyl$_{(C\leq6)}$, such as methyl, isopropyl, or t-butyl, $R_3$ may be alkyl$_{(C\leq6)}$, such as methyl, or $R_3$ may be alkoxy$_{(C\leq6)}$, such as methoxy, or $R_3$ may be aryl$_{(C\leq8)}$, such as phenyl, or $R_3$ may be halo, such as Cl, and/or $R_3$ may be hydrogen. $R_4$ may be halo, such as Cl. $R_3$ and $R_4$ may be taken together and form a second fused phenyl ring. R may be hydrogen. n may be 1, m may be 0 or 1. The compound according may be further defined as:

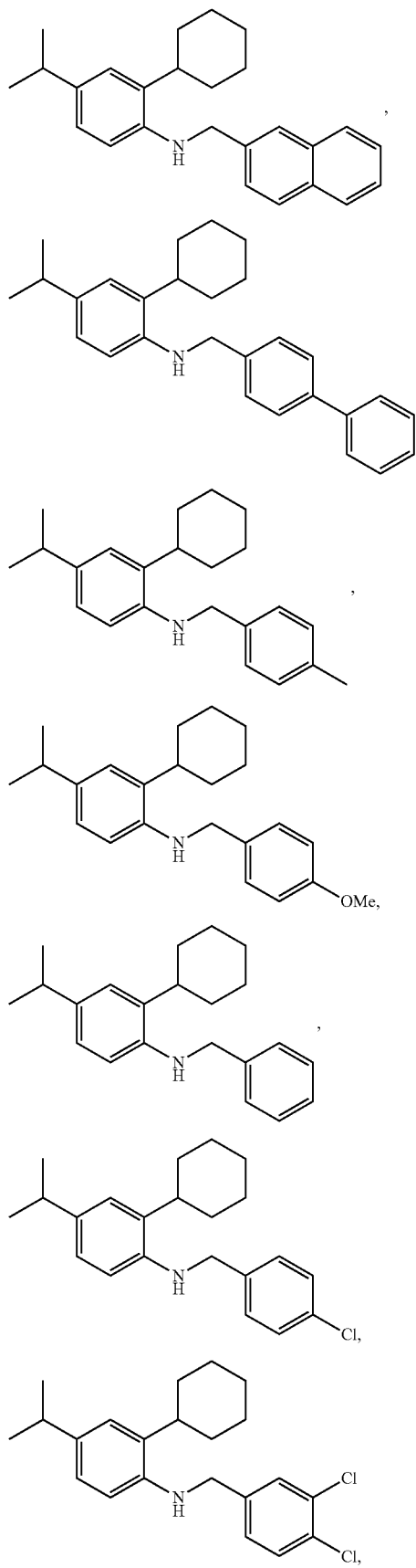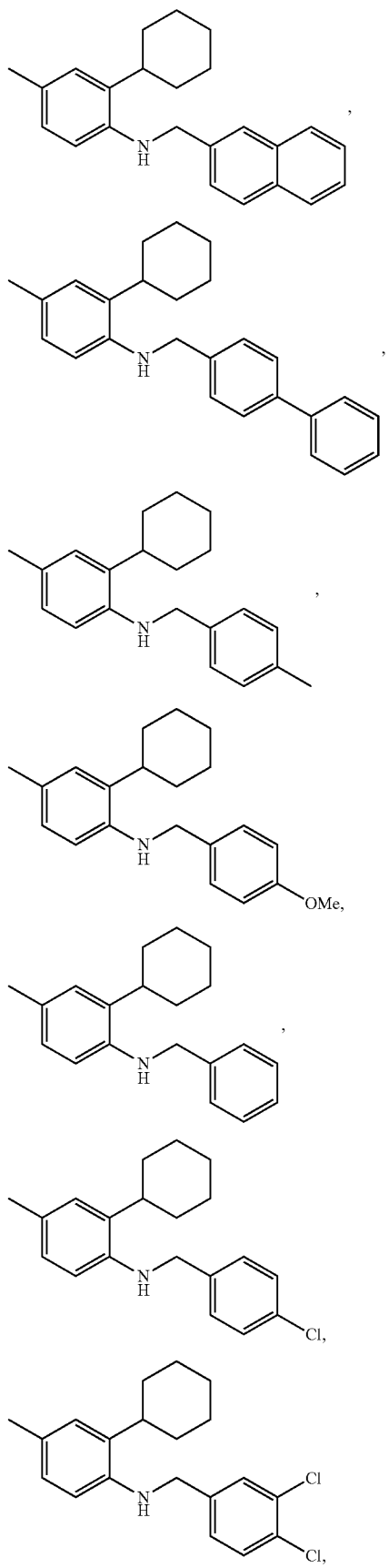

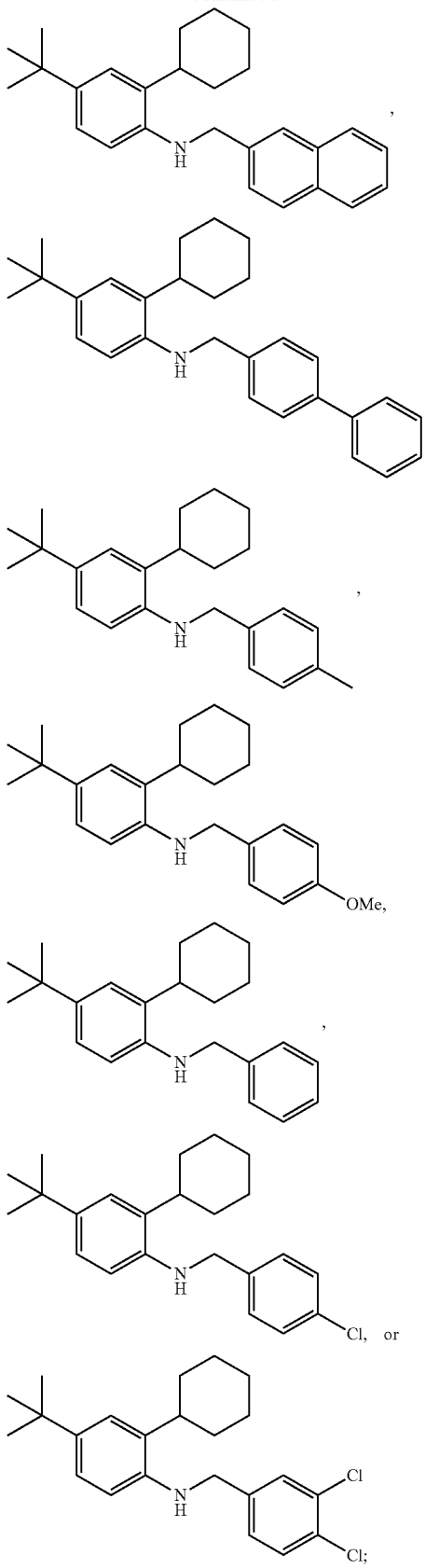

or a pharmaceutically acceptable salt thereof.

Also provided are pharmaceutical compositions comprising (A) a compound as defined above; and (B) an excipient. The pharmaceutical composition may be formulated for administration orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. The pharmaceutical composition may be formulated as a unit dose.

Also provided, there is provided a method of treating a disease or disorder in, or providing for neuroprotection of, a patient in need thereof comprising administering to the patient a therapeutically effective amount of a compound or pharmaceutical composition as defined above. The disease or disorder may be cancer or gallstone disease. The cancer may be hormal cancer, such as breast cancer, including triple negative breast cancer, or leukemia, such as CML, CLL, ALL or AML. The method may further comprise a second anti-cancer therapy. The method may comprise administering the compound or composition once, such as two or more times. The patient may be a mammal, such as a human.

A further embodiment, there is provided a method of modulating the activity of a G protein-coupled estrogen receptor (GPER) comprising contacting the GPER with a compound or a pharmaceutical composition as defined above. The compound or pharmaceutical composition may inhibit the activity of the GPER, such as where the inhibition of the activity of the GPER is sufficient to treat a disease or disorder associated with misregulation of GPER.

Further, there is provided a method of screening a compound for modulation of a G protein-coupled estrogen receptor (GPER) comprising (a) incubating a cell expressing GPER with a calcium indicator; (b) exposing the cell to a first compound; and (c) measuring the change in signal from the calcium indicator, wherein a change in signal is associated with a change in the activity of the GPER. The first compound may be an agonist, and optionally, the first compound may be a known agonist, and the method further comprises exposing the cell to a second compound prior to step (d), where the second compound may be an antagonist. The second compound may be administered before the first compound, or the second compound is administered after the first compound. The calcium indicator may be a synthetic indicator, such as a fluorescent indicator, and the change in signal may be a change in fluorescent intensity. A positive change in signal from the calcium indicator may be indicative of agonism of GPER, and a negative change in signal from the calcium indicator may be indicative of antagonism of GPER. The assay may be performed using no more than about 100,000 cells, and/or the assay may be performed using a multiwell assay format, such as a 24-well, 96-well or 384-well assay format. The cell may be recombinantly engineered to express or overexpress GPER, or the cell may express endogenous GPER or overexpresses endogenous GPER as compared to a non-disease cell. The cell may be a chimera Gqi5, which couples GPER for calcium signaling.

Any embodiment discussed with respect to one aspect of the disclosure applies to other aspects of the disclosure as well.

The embodiments in the Examples section are understood to be embodiments of the disclosure that are applicable to all aspects of the disclosure.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following figures form part of the present specification and are included to further demonstrate certain aspects of the present disclosure. The disclosure may be better understood by reference to one or more of these figures in combination with the detailed description of specific embodiments presented herein.

FIG. 13. $G_s$ pathway in HL-60 cells exhibited a reduction in signal when treated with the $EC_{80}$ value of G-1. For each assay, cells were pretreated with 1 μM forskolin. For antagonists, cells were pretreated with 1 μM forskolin, G-1, and then varying concentrations of the antagonists sequentially. VC=vehicle control. G-36 (**P<0.01) and 8 (*P<0.05) show a statistically significant reduction in inhibition of cAMP formation.

FIGS. 14A-D. Effect of the potent GPR$_{30}$-selective antagonist SG-1 on the formation of E2-induced gallstones. (FIG. 14A) SG-1 significantly reduces, in a dose-dependent manner, gallstone formation in E2-treated OVX mice. (FIG. 14B) Representative photomicrographs of mucin gel, liquid crystals, cholesterol monohydrate crystals, sandy stones, and real gallstones as observed in gallbladder bile of E2-treated OVX mice at week 8 after SG-1 treatment at 0 (top panel), 0.016 (middle panel), and 0.032 mg/day/kg (bottom panel). All magnifications are ×100, except for SG-1 treatment at 0.032 mg/day/kg, which are ×200, by polarizing light microscopy. (FIG. 14C) The relative lipid compositions of pooled gallbladder bile from E2-treated OVX mice treated with various doses of SG-1 from 0 to 0.032 mg/day/kg, as well as fed the lithogenic diet for 8 weeks are plotted on a condensed phase diagram. Because of an 8-week feeding of the lithogenic diet, the relative lipid composition of pooled gallbladder bile from E2-treated OVX mice is located in the central three-phase zone denoted Region C, where at equilibrium the bile is composed of solid cholesterol crystals, liquid crystals, and saturated micelles. By treating mice with varying doses of SG-1, the relative lipid composition of pooled gallbladder bile gradually shifts down. These alterations explain that gallstone prevalence is reduced in these mice treated with SG-1 in a dose-dependent fashion. Relative lipid composition of pooled gallbladder bile from E2-treated OVX mice after an 8-week feeding of the lithogenic diet, as well as treating of SG-1 at the following doses: ●0 mg/day/kg; ▲ 0.016 mg/day/kg; and ■ 0.032 mg/day/kg. (FIG. 14D) Effect of E2 and SG-1 on the expression of Gpr30, Erα, and Erβ in the liver. The data are expressed relative to mRNA levels of Gpr30, Erα, and Erβ in the liver of OVX mice receiving neither E2 nor SG-1, as well as fed the lithogenic diet for 8 weeks, and their relative expression levels are set at 1. Treatment of E2 at 6 μg/day results in a significant increase in mRNA levels of the liver Gpr30 and Erα, but not Erβ genes in OVX mice. Notably, expression of Gpr30 in the liver is significantly reduced by the potent GPR$_{30}$ selective antagonist SG-1 in a dose-dependent manner in OVX mice even treated with E2.

DESCRIPTION OF ILLUSTRATIVE EMBODIMENTS

Figure 1:
FIG. 1 shows the Western blot analysis that shows the presence of GPER in HL-60 cells and illustrates that GPER can be knocked down with specific GPER siRNA.

The inventors have identified small molecules that may interact with and inhibit estrogen binding to GPER. These interactions may signify that inhibition of GPER to block estrogen is an effective method for curbing estrogen promoted cancer cell proliferation. These and other aspects of the disclosure are described in detail below.

I. CALCIUM DISORDERS

A. Cancer

The term cancer defines a group of diseases involving abnormal cell growth with the potential to invade or spread to other parts of the body. Not all tumors are cancerous; benign tumors do not spread to other parts of the body. Possible signs and symptoms include a lump, abnormal bleeding, prolonged cough, unexplained weight loss and a change in bowel movements. While these symptoms may indicate cancer, they may have other causes. Over 100 types of cancers affect humans.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Of particular interest are breast cancer and leukemias, which are discussed further below.

1. Breast Cancer

As discussed above, breast cancer is a world-wide healthy challenge and results in significant mortality across ethnicities and at all socio-economic levels. Breast cancer is a cancer that starts in the breast, usually in the inner lining of the milk ducts or lobules. There are different types of breast cancer, with different stages (spread), aggressiveness, and genetic makeup. With best treatment, 10-year disease-free survival varies from 98% to 10%. Treatment is selected from surgery, drugs (chemotherapy), and radiation.

The first symptom, or subjective sign, of breast cancer is typically a lump that feels different from the surrounding breast tissue. According to the *The Merck Manual*, more than 80% of breast cancer cases are discovered when the woman feels a lump. According to the American Cancer Society, the first medical sign, or objective indication of breast cancer as detected by a physician, is discovered by mammogram. Lumps found in lymph nodes located in the armpits can also indicate breast cancer. Indications of breast cancer other than a lump may include changes in breast size or shape, skin dimpling, nipple inversion, or spontaneous single-nipple discharge. Pain ("mastodynia") is an unreliable tool in determining the presence or absence of breast cancer, but may be indicative of other breast health issues.

When breast cancer cells invade the dermal lymphatics—small lymph vessels in the skin of the breast—its presentation can resemble skin inflammation and thus is known as inflammatory breast cancer (IBC). Symptoms of inflammatory breast cancer include pain, swelling, warmth and redness throughout the breast, as well as an orange-peel texture to the skin referred to as "peau d'orange." Another reported symptom complex of breast cancer is Paget's disease of the breast. This syndrome presents as eczematoid skin changes such as redness and mild flaking of the nipple skin. As Paget's advances, symptoms may include tingling, itching, increased sensitivity, burning, and pain. There may also be discharge from the nipple. Approximately half of women diagnosed with Paget's also have a lump in the breast.

Occasionally, breast cancer presents as metastatic disease, that is, cancer that has spread beyond the original organ. Metastatic breast cancer will cause symptoms that depend on the location of metastasis. Common sites of metastasis include bone, liver, lung and brain. Unexplained weight loss can occasionally herald an occult breast cancer, as can symptoms of fevers or chills. Bone or joint pains can sometimes be manifestations of metastatic breast cancer, as can jaundice or neurological symptoms. These symptoms are "non-specific," meaning they can also be manifestations of many other illnesses.

The primary risk factors that have been identified are sex, age, childbearing, hormones, a high-fat diet, alcohol intake, obesity, and environmental factors such as tobacco use, radiation and shiftwork. No etiology is known for 95% of breast cancer cases, while approximately 5% of new breast cancers are attributable to hereditary syndromes. In particular, carriers of the breast cancer susceptibility genes, BRCA1 and BRCA2, are at a 30-40% increased risk for breast and ovarian cancer, depending on in which portion of the protein the mutation occurs. Experts believe that 95% of inherited breast cancer can be traced to one of these two genes. Hereditary breast cancers can take the form of a site-specific hereditary breast cancer—cancers affecting the breast only—or breast—ovarian and other cancer syndromes. Breast cancer can be inherited both from female and male relatives.

Breast cancer subtypes are typically categorized on an immunohistochemical basis. Subtype definitions are generally as follows:
  normal (ER+, PR+, HER2+, cytokeratin 5/6+, and HER1+)
  luminal A (ER+ and/or PR+, HER2−)
  luminal B (ER+ and/or PR+, HER2+)
  triple-negative (ER−, PR−, HER2−)
  HER2+/ER−(ER−, PR−, and HER2+)
  unclassified (ER−, PR−, HER2−, cytokeratin 5/6−, and HER1−)

In the case of triple-negative breast cancer cells, the cancer's growth is not driven by estrogen or progesterone, or by growth signals coming from the $HER_2$ protein. By the same token, such cancer cells do not respond to hormonal therapy, such as tamoxifen or aromatase inhibitors, or therapies that target $HER_2$ receptors, such as Herceptin®. About 10-20% of breast cancers are found to be triple-negative. It is important to identify these types of cancer so that one can avoid costly and toxic effects of therapies that are unlike to succeed, and to focus on treatments that can be used to treat triple-negative breast cancer. Like other forms of breast cancer, triple-negative breast cancer can be treated with surgery, radiation therapy, and/or chemotherapy. One particularly promising approach is "neoadjuvant" therapy, where chemo- and/or radiotherapy is provided prior to surgery. Another drug therapy is the use of poly (ADP-ribose) polymerase, or PARP inhibitors.

While screening techniques discussed above are useful in determining the possibility of cancer, a further testing is necessary to confirm whether a lump detected on screening is cancer, as opposed to a benign alternative such as a simple cyst. In a clinical setting, breast cancer is commonly diagnosed using a "triple test" of clinical breast examination (breast examination by a trained medical practitioner), mammography, and fine needle aspiration cytology. Both mammography and clinical breast exam, also used for screening, can indicate an approximate likelihood that a lump is cancer, and may also identify any other lesions. Fine Needle Aspiration and Cytology (FNAC), performed as an outpatient procedure using local anaesthetic, involves attempting to extract a small portion of fluid from the lump. Clear fluid makes the lump highly unlikely to be cancerous, but bloody fluid may be sent off for inspection under a microscope for cancerous cells. Together, these three tools can be used to diagnose breast cancer with a good degree of accuracy. Other options for biopsy include core biopsy, where a section of the breast lump is removed, and an excisional biopsy, where the entire lump is removed.

Breast cancer screening is an attempt to find cancer in otherwise healthy individuals. The most common screening method for women is a combination of x-ray mammography and clinical breast exam. In women at higher than normal risk, such as those with a strong family history of cancer, additional tools may include genetic testing or breast Magnetic Resonance Imaging.

Breast self-examination was a form of screening that was heavily advocated in the past, but has since fallen into disfavour since several large studies have shown that it does not have a survival benefit for women and often causes considerably anxiety. This is thought to be because cancers that could be detected tended to be at a relatively advanced stage already, whereas other methods push to identify the cancer at an earlier stage where curative treatment is more often possible.

X-ray mammography uses x-rays to examine the breast for any uncharacteristic masses or lumps. Regular mammograms are recommended in several countries in women over a certain age as a screening tool.

Genetic testing for breast cancer typically involves testing for mutations in the BRCA genes. This is not generally a recommended technique except for those at elevated risk for breast cancer.

The mainstay of breast cancer treatment is surgery when the tumor is localized, with possible adjuvant hormonal therapy (with tamoxifen or an aromatase inhibitor), chemotherapy, and/or radiotherapy. At present, the treatment recommendations after surgery (adjuvant therapy) follow a pattern. Depending on clinical criteria (age, type of cancer, size, metastasis) patients are roughly divided into high risk and low risk cases, with each risk category following different rules for therapy. Treatment possibilities include radiation therapy, chemotherapy, hormone therapy, and immune therapy.

Targeted cancer therapies are treatments that target specific characteristics of cancer cells, such as a protein that allows the cancer cells to grow in a rapid or abnormal way. Targeted therapies are generally less likely than chemotherapy to harm normal, healthy cells. Some targeted therapies are antibodies that work like the antibodies made naturally by one's immune system. These types of targeted therapies are sometimes called immune-targeted therapies.

There are currently 3 targeted therapies doctors use to treat breast cancer. Herceptin® (trastuzumab) works against HER2-positive breast cancers by blocking the ability of the cancer cells to receive chemical signals that tell the cells to grow. Tykerb® (lapatinib) works against HER2-positive breast cancers by blocking certain proteins that can cause uncontrolled cell growth. Avastin® (bevacizumab) works by blocking the growth of new blood vessels that cancer cells depend on to grow and function.

Hormonal (anti-estrogen) therapy works against hormone-receptor-positive breast cancer in two ways: first, by lowering the amount of the hormone estrogen in the body, and second, by blocking the action of estrogen in the body. Most of the estrogen in women's bodies is made by the ovaries. Estrogen makes hormone-receptor-positive breast cancers grow. So reducing the amount of estrogen or blocking its action can help shrink hormone-receptor-positive breast cancers and reduce the risk of hormone-receptor-positive breast cancers coming back (recurring). Hormonal therapy medicines are not effective against hormone-receptor-negative breast cancers.

There are several types of hormonal therapy medicines, including aromatase inhibitors, selective estrogen receptor modulators, and estrogen receptor downregulators. In some cases, the ovaries and fallopian tubes may be surgically removed to treat hormone-receptor-positive breast cancer or as a preventive measure for women at very high risk of breast cancer. The ovaries also may be shut down temporarily using medication.

In planning treatment, doctors can also use PCR tests like Oncotype DX or microarray tests that predict breast cancer recurrence risk based on gene expression. In February 2007, the first breast cancer predictor test won formal approval from the Food and Drug Administration. This is a new gene test to help predict whether women with early-stage breast cancer will relapse in 5 or 10 years, this could help influence how aggressively the initial tumor is treated.

Radiation therapy is also used to help destroy cancer cells that may linger after surgery. Radiation can reduce the risk of recurrence by 50-66% when delivered in the correct dose.

2. Leukemia

Leukemia, also spelled leukaemia, is a group of cancers that usually begin in the bone marrow and result in high numbers of abnormal white blood cells. These white blood cells are not fully developed and are called blasts or leukemia cells. Symptoms may include bleeding and bruising problems, feeling tired, fever, and an increased risk of infections. These symptoms occur due to a lack of normal blood cells. Diagnosis is typically made by blood tests or bone marrow biopsy.

The exact cause of leukemia is unknown. Different kinds of leukemia are believed to have different causes. Both inherited and environmental (non-inherited) factors are believed to be involved. Risk factors include smoking, ionizing radiation, some chemicals (such as benzene), prior chemotherapy, and Down syndrome. People with a family history of leukemia are also at higher risk. There are four main types of leukemia—acute lymphoblastic leukemia (ALL), acute myeloid leukemia (AML), chronic lymphocytic leukemia (CLL) and chronic myeloid leukemia (CML)—as well as a number of less common types. Leukemias and lymphomas both belong to a broader group of tumors that affect the blood, bone marrow, and lymphoid system, known as tumors of the hematopoietic and lymphoid tissues.

Treatment may involve some combination of chemotherapy, radiation therapy, targeted therapy, and bone marrow transplant, in addition to supportive care and palliative care as needed. Certain types of leukemia may be managed with watchful waiting. The success of treatment depends on the type of leukemia and the age of the person. Outcomes have improved in the developed world. The average five-year survival rate is 57% in the United States. In children under 15, the five-year survival rate is greater than 60 to 85%, depending on the type of leukemia. In children with acute leukemia who are cancer-free after five years, the cancer is unlikely to return.

In 2012, leukemia developed in 352,000 people globally and caused 265,000 deaths. It is the most common type of cancer in children, with three quarters of leukemia cases in children being the acute lymphoblastic type. However, about 90% of all leukemias are diagnosed in adults, with AML and CLL being most common in adults. It occurs more commonly in the developed world.

Clinically and pathologically, leukemia is subdivided into a variety of large groups. The first division is between its acute and chronic forms. Acute leukemia is characterized by a rapid increase in the number of immature blood cells. The crowding that results from such cells makes the bone marrow unable to produce healthy blood cells. Immediate treatment is required in acute leukemia because of the rapid progression and accumulation of the malignant cells, which then spill over into the bloodstream and spread to other organs of the body. Acute forms of leukemia are the most common forms of leukemia in children.

In contrast, chronic leukemia is characterized by the excessive buildup of relatively mature, but still abnormal, white blood cells. Typically taking months or years to progress, the cells are produced at a much higher rate than normal, resulting in many abnormal white blood cells. Whereas acute leukemia must be treated immediately, chronic forms are sometimes monitored for some time before treatment to ensure maximum effectiveness of therapy. Chronic leukemia mostly occurs in older people, but can occur in any age group.

Additionally, the diseases are subdivided according to which kind of blood cell is affected. This divides leukemias into lymphoblastic or lymphocytic leukemias and myeloid or myelogenous leukemias.

In lymphoblastic or lymphocytic leukemias, the cancerous change takes place in a type of marrow cell that normally goes on to form lymphocytes, which are infection-fighting immune system cells. Most lymphocytic leukemias involve a specific subtype of lymphocyte, the B cell.

In myeloid or myelogenous leukemias, the cancerous change takes place in a type of marrow cell that normally goes on to form red blood cells, some other types of white cells, and platelets.

Combining these two classifications provides a total of four main categories. Within each of these main categories, there are typically several subcategories. Finally, some rarer types are usually considered to be outside of this classification scheme.

Acute lymphoblastic leukemia (ALL) is the most common type of leukemia in young children. It also affects adults, especially those 65 and older. Standard treatments involve chemotherapy and radiotherapy. The survival rates vary by age: 85% in children and 50% in adults. Subtypes include precursor B acute lymphoblastic leukemia, precursor T acute lymphoblastic leukemia, Burkitt's leukemia, and acute biphenotypic leukemia.

Chronic lymphocytic leukemia (CLL) most often affects adults over the age of 55. It sometimes occurs in younger adults, but it almost never affects children. Two-thirds of affected people are men. The five-year survival rate is 75%. It is incurable, but there are many effective treatments. One subtype is B-cell prolymphocytic leukemia, a more aggressive disease.

Acute myelogenous leukemia (AML) occurs more commonly in adults than in children, and more commonly in men than women. It is treated with chemotherapy. The five-year survival rate is 40%, except for APL (Acute Promyelocytic Leukemia), which has a survival rate greater than 90%. Subtypes of AML include acute promyelocytic leukemia, acute myeloblastic leukemia, and acute megakaryoblastic leukemia.

Chronic myelogenous leukemia (CML) occurs mainly in adults; a very small number of children also develop this disease. It is treated with imatinib (Gleevec in United States, Glivec in Europe) or other drugs. The five-year survival rate is 90%. One subtype is chronic myelomonocytic leukemia.

Hairy cell leukemia (HCL) is sometimes considered a subset of chronic lymphocytic leukemia, but does not fit neatly into this category. About 80% of affected people are adult men. No cases in children have been reported. HCL is incurable but easily treatable. Survival is 96% to 100% at ten years.

T-cell prolymphocytic leukemia (T-PLL) is a very rare and aggressive leukemia affecting adults; somewhat more men than women are diagnosed with this disease. Despite its overall rarity, it is the most common type of mature T cell leukemia; nearly all other leukemias involve B cells. It is difficult to treat, and the median survival is measured in months.

Large granular lymphocytic leukemia may involve either T-cells or NK cells; like hairy cell leukemia, which involves solely B cells, it is a rare and indolent (not aggressive) leukemia.

Adult T-cell leukemia is caused by human T-lymphotropic virus (HTLV), a virus similar to HIV. Like HIV, HTLV infects CD4+ T-cells and replicates within them; however, unlike HIV, it does not destroy them. Instead, HTLV "immortalizes" the infected T-cells, giving them the ability to proliferate abnormally. Human T-cell lymphotropic virus types I and II (HTLV-I/II) are endemic in certain areas of the world.

The most common symptoms in children are easy bruising, pale skin, fever, and an enlarged spleen or liver.

Damage to the bone marrow, by way of displacing the normal bone marrow cells with higher numbers of immature white blood cells, results in a lack of blood platelets, which are important in the blood clotting process. This means people with leukemia may easily become bruised, bleed excessively, or develop pinprick bleeds (petechiae).

White blood cells, which are involved in fighting pathogens, may be suppressed or dysfunctional. This could cause the patient's immune system to be unable to fight off a simple infection or to start attacking other body cells. Because leukemia prevents the immune system from working normally, some patients experience frequent infection, ranging from infected tonsils, sores in the mouth, or diarrhea to life-threatening pneumonia or opportunistic infections.

Finally, the red blood cell deficiency leads to anemia, which may cause dyspnea and pallor.

Some patients experience other symptoms, such as feeling sick, having fevers, chills, night sweats, feeling fatigued and other flu-like symptoms. Some patients experience nausea or a feeling of fullness due to an enlarged liver and spleen; this can result in unintentional weight loss. Blasts affected by the disease may come together and become swollen in the liver or in the lymph nodes causing pain and leading to nausea.

If the leukemic cells invade the central nervous system, then neurological symptoms (notably headaches) can occur. Uncommon neurological symptoms like migraines, seizures, or coma can occur as a result of brain stem pressure. All symptoms associated with leukemia can be attributed to other diseases. Consequently, leukemia is always diagnosed through medical tests.

The word leukemia, which means 'white blood', is derived from the characteristic high white blood cell count that presents in most afflicted patients before treatment. The high number of white blood cells are apparent when a blood sample is viewed under a microscope, with the extra white blood cells frequently being immature or dysfunctional. The excessive number of cells can also interfere with the level of other cells, causing further harmful imbalance in the blood count.

Some leukemia patients do not have high white blood cell counts visible during a regular blood count. This less-common condition is called aleukemia. The bone marrow still contains cancerous white blood cells which disrupt the normal production of blood cells, but they remain in the marrow instead of entering the bloodstream, where they would be visible in a blood test. For an aleukemic patient, the white blood cell counts in the bloodstream can be normal or low. Aleukemia can occur in any of the four major types of leukemia, and is particularly common in hairy cell leukemia.

There is no single known cause for any of the different types of leukemias. The few known causes, which are not generally factors within the control of the average person, account for relatively few cases. The cause for most cases of leukemia is unknown. The different leukemias likely have different causes.

Leukemia, like other cancers, results from mutations in the DNA. Certain mutations can trigger leukemia by activating oncogenes or deactivating tumor suppressor genes, and thereby disrupting the regulation of cell death, differentiation or division. These mutations may occur spontaneously or as a result of exposure to radiation or carcinogenic substances.

Among adults, the known causes are natural and artificial ionizing radiation, a few viruses such as human T-lymphotropic virus, and some chemicals, notably benzene and alkylating chemotherapy agents for previous malignancies. Use of tobacco is associated with a small increase in the risk of developing acute myeloid leukemia in adults. Cohort and case-control studies have linked exposure to some petrochemicals and hair dyes to the development of some forms of leukemia. Diet has very limited or no effect, although eating more vegetables may confer a small protective benefit.

Viruses have also been linked to some forms of leukemia. For example, human T-lymphotropic virus (HTLV-1) causes adult T-cell leukemia.

A few cases of maternal-fetal transmission (a baby acquires leukemia because its mother had leukemia during the pregnancy) have been reported. Children born to mothers who use fertility drugs to induce ovulation are more than twice as likely to develop leukemia during their childhoods than other children.

Large doses of Sr-90 emission from nuclear reactors, nicknamed bone seeker increases the risk of bone cancer and leukemia in animals, and is presumed to do so in people.

Some people have a genetic predisposition towards developing leukemia. This predisposition is demonstrated by family histories and twin studies. The affected people may have a single gene or multiple genes in common. In some cases, families tend to develop the same kinds of leukemia as other members; in other families, affected people may develop different forms of leukemia or related blood cancers.

In addition to these genetic issues, people with chromosomal abnormalities or certain other genetic conditions have a greater risk of leukemia. For example, people with Down syndrome have a significantly increased risk of developing forms of acute leukemia (especially acute myeloid leukemia), and Fanconi anemia is a risk factor for developing acute myeloid leukemia. Mutation in SPRED1 gene has been associated with a predisposition to childhood leukemia.

Chronic myelogenous leukemia is associated with a genetic abnormality called the Philadelphia translocation; 95% of people with CML carry the Philadelphia mutation, although this is not exclusive to CML and can be observed in people with other types of leukemia.

Whether or not non-ionizing radiation causes leukemia has been studied for several decades. The International Agency for Research on Cancer expert working group undertook a detailed review of all data on static and extremely low frequency electromagnetic energy, which occurs naturally and in association with the generation, transmission, and use of electrical power. They concluded that there is limited evidence that high levels of ELF magnetic (but not electric) fields might cause some cases of childhood leukemia. No evidence for a relationship to leukemia or another form of malignancy in adults has been demonstrated. Since exposure to such levels of ELFs is relatively uncommon, the World Health Organization concludes that ELF exposure, if later proven to be causative, would account for just 100 to 2400 cases worldwide each year, representing 0.2 to 4.9% of the total incidence of childhood leukemia for that year (about 0.03 to 0.9% of all leukemias).

Diagnosis is usually based on repeated complete blood counts and a bone marrow examination following observations of the symptoms. Sometimes, blood tests may not show that a person has leukemia, especially in the early stages of the disease or during remission. A lymph node biopsy can be performed to diagnose certain types of leukemia in certain situations.

Following diagnosis, blood chemistry tests can be used to determine the degree of liver and kidney damage or the effects of chemotherapy on the patient. When concerns arise about other damage due to leukemia, doctors may use an X-ray, MRI, or ultrasound. These can potentially show leukemia's effects on such body parts as bones (X-ray), the brain (MRI), or the kidneys, spleen, and liver (ultrasound). CT scans can be used to check lymph nodes in the chest, though this is uncommon.

Despite the use of these methods to diagnose whether or not a patient has leukemia, many people have not been diagnosed because many of the symptoms are vague, non-specific, and can refer to other diseases. For this reason, the American Cancer Society estimates that at least one-fifth of the people with leukemia have not yet been diagnosed.

Most forms of leukemia are treated with pharmaceutical medication, typically combined into a multi-drug chemotherapy regimen. Some are also treated with radiation therapy. In some cases, a bone marrow transplant is effective.

Management of ALL is directed towards control of bone marrow and systemic (whole-body) disease. Additionally, treatment must prevent leukemic cells from spreading to other sites, particularly the central nervous system (CNS), e.g., monthly lumbar punctures. In general, ALL treatment is divided into several phases:

Induction chemotherapy to bring about bone marrow remission. For adults, standard induction plans include prednisone, vincristine, and an anthracycline drug; other drug plans may include L-asparaginase or cyclophosphamide. For children with low-risk ALL, standard therapy usually consists of three drugs (prednisone, L-asparaginase, and vincristine) for the first month of treatment.

Consolidation therapy or intensification therapy to eliminate any remaining leukemia cells. There are many different approaches to consolidation, but it is typically a high-dose, multi-drug treatment that is undertaken for a few months.

Patients with low- to average-risk ALL receive therapy with antimetabolite drugs such as methotrexate and 6-mercaptopurine (6-MP). High-risk patients receive higher drug doses of these drugs, plus additional drugs.

CNS prophylaxis (preventive therapy) to stop the cancer from spreading to the brain and nervous system in high-risk patients. Standard prophylaxis may include radiation of the head and/or drugs delivered directly into the spine.

Maintenance treatments with chemotherapeutic drugs to prevent disease recurrence once remission has been achieved. Maintenance therapy usually involves lower drug doses, and may continue for up to three years.

Alternatively, allogeneic bone marrow transplantation may be appropriate for high-risk or relapsed patients.

Hematologists base CLL treatment on both the stage and symptoms of the individual patient. A large group of CLL patients have low-grade disease, which does not benefit from treatment. Individuals with CLL-related complications or more advanced disease often benefit from treatment. In general, the indications for treatment are:

falling hemoglobin or platelet count
progression to a later stage of disease
painful, disease-related overgrowth of lymph nodes or spleen
an increase in the rate of lymphocyte production For most people with CLL, it is incurable by present treatments, so treatment is directed towards suppressing the disease for many years, rather than totally and permanently eliminating it. The primary chemotherapeutic plan is combination chemotherapy with chlorambucil or cyclophosphamide, plus a corticosteroid such as prednisone or prednisolone. The use of a corticosteroid has the additional benefit of suppressing some related autoimmune diseases, such as immunohemolytic anemia or immune-mediated thrombocytopenia. In resistant cases, single-agent treatments with nucleoside drugs such as fludarabine, pentostatin, or cladribine may be successful. Younger and healthier patients may choose allogeneic or autologous bone marrow transplantation in the hope of a permanent cure.

Many different anti-cancer drugs are effective for the treatment of AML. Treatments vary somewhat according to the age of the patient and according to the specific subtype of AML. Overall, the strategy is to control bone marrow and systemic (whole-body) disease, while offering specific treatment for the central nervous system (CNS), if involved.

In general, most oncologists rely on combinations of drugs for the initial, induction phase of chemotherapy. Such combination chemotherapy usually offers the benefits of early remission and a lower risk of disease resistance. Consolidation and maintenance treatments are intended to prevent disease recurrence. Consolidation treatment often entails a repetition of induction chemotherapy or the intensification chemotherapy with additional drugs. By contrast, maintenance treatment involves drug doses that are lower than those administered during the induction phase.

There are many possible treatments for CML, but the standard of care for newly diagnosed patients is imatinib (Gleevec) therapy. Compared to most anti-cancer drugs, it has relatively few side effects and can be taken orally at home. With this drug, more than 90% of patients will be able to keep the disease in check for at least five years, so that CML becomes a chronic, manageable condition.

In a more advanced, uncontrolled state, when the patient cannot tolerate imatinib, or if the patient wishes to attempt a permanent cure, then an allogeneic bone marrow transplantation may be performed. This procedure involves high-dose chemotherapy and radiation followed by infusion of bone marrow from a compatible donor. Approximately 30% of patients die from this procedure.

Patients with hairy cell leukemia who are symptom-free typically do not receive immediate treatment. Treatment is generally considered necessary when the patient shows signs and symptoms such as low blood cell counts (e.g., infection-fighting neutrophil count below 1.0 K/μL), frequent infections, unexplained bruises, anemia, or fatigue that is significant enough to disrupt the patient's everyday life.

Patients who need treatment usually receive either one week of cladribine, given daily by intravenous infusion or a simple injection under the skin, or six months of pentostatin, given every four weeks by intravenous infusion. In most cases, one round of treatment will produce a prolonged remission.

Other treatments include rituximab infusion or self-injection with Interferon-alpha. In limited cases, the patient may benefit from splenectomy (removal of the spleen). These treatments are not typically given as the first treatment because their success rates are lower than cladribine or pentostatin.

Most patients with T-cell prolymphocytic leukemia, a rare and aggressive leukemia with a median survival of less than one year, require immediate treatment.

T-cell prolymphocytic leukemia is difficult to treat, and it does not respond to most available chemotherapeutic drugs. Many different treatments have been attempted, with limited success in certain patients: purine analogues (pentostatin, fludarabine, cladribine), chlorambucil, and various forms of combination chemotherapy (cyclophosphamide, doxorubicin, vincristine, prednisone CHOP, cyclophosphamide, vincristine, prednisone [COP], vincristine, doxorubicin, prednisone, etoposide, cyclophosphamide, bleomycin VAPEC-B). Alemtuzumab (Campath), a monoclonal antibody that attacks white blood cells, has been used in treatment with greater success than previous options.

Some patients who successfully respond to treatment also undergo stem cell transplantation to consolidate the response.

Treatment for juvenile myelomonocytic leukemia can include splenectomy, chemotherapy, and bone marrow transplantation.

B. Gallstone Disease

Gallstone disease refers to the condition where gallstones are either in the gallbladder or common bile duct. The presence of stones in the gallbladder is referred to as cholelithiasis. If gallstones migrate into the ducts of the biliary tract, the condition is referred to as choledocholithiasis. Choledocholithiasis is frequently associated with obstruction of the biliary tree, which in turn can lead to acute ascending cholangitis, a serious infection of the bile ducts. Gallstones within the ampulla of Vater can obstruct the exocrine system of the pancreas, which in turn can result in pancreatitis.

A gallstone is a stone formed within the gallbladder out of bile components. The term cholelithiasis may refer to the presence of stones in the gallbladder or to the diseases caused by gallstones. Most people with gallstones (about 80%) never have symptoms. In 1-4% of those with gallstones, a crampy pain in the right upper part of the abdomen, known as biliary colic, occurs each year. Complications of gallstones include inflammation of the gallbladder, inflammation of the pancreas, and liver inflammation. Symptoms of these complications may include pain of more than five hours duration, fever, yellowish skin, vomiting, or tea-color urine.

Risk factors for gallstones include birth control pills, pregnancy, a family history of gallstones, obesity, diabetes, liver disease, or rapid weight loss. Gallstones are formed in the gallbladder, typically from either cholesterol or bilirubin. Gallstones may be suspected based on symptoms. Diagnosis is then typically confirmed by ultrasound. Complications may be detected on blood tests.

Prevention is by maintaining a healthy weight and eating a diet high in fiber and low in simple carbohydrates. If there are no symptoms, treatment is usually not needed. In those who are having gallbladder attacks surgery to remove the gallbladder is typically recommended. This can be either done through several small incisions or through a single larger incision. Surgery is typically done under general anesthesia. In those who are unable to have surgery, medication to try to dissolve the stones or shock wave lithotripsy may be tried.

In the developed world, 10-15% of adults have gallstones. Rates in many parts of Africa, however, are as low as 3%. Gallbladder and biliary related diseases occurred in about 104 million people (1.6%) in 2013 and they resulted in 106,000 deaths. Women more commonly have stones than men and they occur more commonly after the age of 40. Certain ethnic groups have gallstones more often than others. For example, 48% of American Indians have gallstones. Once the gallbladder is removed, outcomes are generally good.

Gallstones may be asymptomatic, even for years. These gallstones are called "silent stones" and do not require treatment. The size and number of gallstones present does not appear to influence whether or not people are symptomatic or asymptomatic. A characteristic symptom of gallstones is a gallstone attack, in which a person may experience colicky pain in the upper-right side of the abdomen, often accompanied by nausea and vomiting, that steadily increases for approximately 30 minutes to several hours. A person may also experience referred pain between the shoulder blades or below the right shoulder. These symptoms may resemble those of a "kidney stone attack". Often, attacks occur after a particularly fatty meal and almost always happen at night, and after drinking.

In addition to pain, nausea, and vomiting, a person may experience a fever. If the stones block the duct and cause bilirubin to leak into the bloodstream and surrounding tissue, there may also be jaundice and itching. This can also lead to confusion. If this is the case, the liver enzymes are likely to be raised.

Rarely, in cases of severe inflammation, gallstones may erode through the gallbladder into adherent bowel potentially causing an obstruction termed gallstone ileus.

Other complications include ascending cholangitis if there is a bacterial infection which can cause purulent inflammation in the biliary tree and liver, and acute pancreatitis as blockage of the bile ducts can prevent active enzymes being secreted into the bowel, instead damaging the pancreas.

Gallstone risk increases for females (especially before menopause) and for people near or above 40 years; the condition is more prevalent among both North and South Americans and among those of European descent than among other ethnicities. A lack of melatonin could significantly contribute to gallbladder stones, as melatonin inhibits cholesterol secretion from the gallbladder, enhances the conversion of cholesterol to bile, and is an antioxidant, which is able to reduce oxidative stress to the gallbladder. Researchers believe that gallstones may be caused by a combination of factors, including inherited body chemistry, body weight, gallbladder motility (movement), and low calorie diet. The absence of such risk factors does not, however, preclude the formation of gallstones.

Nutritional factors that may increase risk of gallstones include constipation; eating fewer meals per day; low intake of the nutrients folate, magnesium, calcium, and vitamin C; low fluid consumption; and, at least for men, a high intake of carbohydrate, a high glycemic load, and high glycemic index diet. Wine and whole-grained bread may decrease the risk of gallstones.

Rapid weight loss increases risk of gallstones. Patients taking orlistat, a weight loss drug, may already be at increased risk for the formation of gall stones. Weight loss with orlistat can increase the risk of gall stones. On the contrary, ursodeoxycholic acid (UCDA), a bile acid, also a drug marketed as Ursodiol, appears to prevent formation of gallstones during weight loss. A high fat diet during weight loss also appears to prevent gallstones.

Cholecystokinin deficiency caused by celiac disease increases risk of gallstone formation, especially when diagnosis of celiac disease is delayed.

Pigment gallstones are most commonly seen in the developing world. Risk factors for pigment stones include hemolytic anemias (such as from sickle-cell disease and hereditary spherocytosis), cirrhosis, and biliary tract infections. People with erythropoietic protoporphyria (EPP) are at increased risk to develop gallstones. Additionally, prolonged use of proton pump inhibitors has been shown to decrease gallbladder function, potentially leading to gallstone formation.

Cholesterol gallstones develop when bile contains too much cholesterol and not enough bile salts. Besides a high concentration of cholesterol, two other factors are important in causing gallstones. The first is how often and how well the gallbladder contracts; incomplete and infrequent emptying of the gallbladder may cause the bile to become overconcentrated and contribute to gallstone formation. This can be caused by high resistance to the flow of bile out of the gallbladder due to the complicated internal geometry of the cystic duct. The second factor is the presence of proteins in the liver and bile that either promote or inhibit cholesterol crystallization into gallstones. In addition, increased levels of the hormone estrogen, as a result of pregnancy or hormone therapy, or the use of combined (estrogen-containing) forms of hormonal contraception, may increase cholesterol levels in bile and also decrease gallbladder movement, resulting in gallstone formation.

Cholecystectomy (gallbladder removal) has a 99% chance of eliminating the recurrence of cholelithiasis. Surgery is only indicated in symptomatic patients. The lack of a gallbladder may have no negative consequences in many people. However, there is a portion of the population—between 10 and 15%—who develop a condition called postcholecystectomy syndrome which may cause gastrointestinal distress and persistent pain in the upper-right abdomen, as well as a 10% risk of developing chronic diarrhea.

There are two surgical options for cholecystectomy. Open cholecystectomy is performed via an abdominal incision (laparotomy) below the lower right ribs. Recovery typically requires 3-5 days of hospitalization, with a return to normal diet a week after release and to normal activity several weeks after release.

Laparoscopic cholecystectomy, introduced in the 1980s, is performed via three to four small puncture holes for a camera and instruments. Post-operative care typically includes a same-day release or a one night hospital stay, followed by a few days of home rest and pain medication. Laparoscopic cholecystectomy patients can, in general, resume normal diet and light activity a week after release, with some decreased energy level and minor residual pain continuing for a month or two. Studies have shown that this procedure is as effective as the more invasive open cholecystectomy, provided the stones are accurately located by cholangiogram prior to the procedure so that they can all be removed.

Cholesterol gallstones can sometimes be dissolved with ursodeoxycholic acid taken by mouth, but it may be necessary for the person to take this medication for years. Gallstones may recur, however, once the drug is stopped. Obstruction of the common bile duct with gallstones can sometimes be relieved by endoscopic retrograde sphincterotomy (ERS) following endoscopic retrograde cholangiopancreatography (ERCP). Gallstones can be broken up using a procedure called extracorporeal shock wave lithotripsy (often simply called "lithotripsy"), which is a method of concentrating ultrasonic shock waves onto the stones to break them into tiny pieces. They are then passed safely in the feces. However, this form of treatment is suitable only when there is a small number of gallstones.

C. Neuroprotection

Accordingly, the compounds of the present disclosure are useful in the treatment or alleviation of neurodegenerative disorders, such as Alzheimer's disease, Parkinson's disease, Lou Gehrig's disease, or multiple sclerosis, to name a few, not to mention central or peripheral nervous system damage, dysfunction, or complications involving same stemming from edema, injury, or trauma. Such damage, dysfunction, or complications may be characterized by an apparent neurological, neurodegenerative, physiological, psychological, or behavioral aberrations, the symptoms of which can be reduced by the administration of a therapeutically effective amount of the compounds of the present invention.

For example, Parkinson's disease (PD) is characterized by a selective degeneration of nigrostriatal dopaminergic pathway. Estrogen neuroprotective effects have been shown in several studies; however, the mechanisms responsible by these effects are still unclear. There is some evidence that glial cell line-derived neurotrophic factor (GDNF) is crucial to the dopaminergic protection provided by 17β-estradiol, and also suggest that the intracellular estrogen receptors (ERs) are not required for that neuroprotective effects. GPER activation has been shown to protect dopaminergic neurons from MPP toxicity in an extent similar to the promoted by a 17β-estradiol. Moreover, GPER activation promotes an increase in GDNF levels, and GDNF antibody neutralization and RNA interference-mediated GDNF knockdown prevented the GPER-mediated dopaminergic protection. Thus, selective agonists of GPER are able to protect dopaminergic neurons, and GDNF overexpression is a key feature to GPER induced the neuroprotective effects.

II. GPER

G protein-coupled estrogen receptor 1 (GPER), also known as G protein-coupled receptor 30 (GPR30), is a protein that in humans is encoded by the GPER gene. GPER binds to and is activated by the female sex hormone estradiol and is responsible for some of the rapid effects that estradiol has on cells.

The classical estrogen receptors first characterized in 1958 are water-soluble proteins located in the interior of cells that are activated by estrogenic hormones such as estradiol and several of its metabolites such as estrone or estriol. These proteins belong to the nuclear hormone receptor class of transcription factors that regulate gene transcription. Since it takes time for genes to be transcribed into RNA and translated into protein, the effects of estrogens binding to these classical estrogen receptors is delayed. However, estrogens are also known to have effects that are too fast to be caused by regulation of gene transcription. In 2005, it was discovered that a member of the G protein-coupled receptor (GPCR) family, GPR30 also binds with high affinity to estradiol and is responsible in part for the rapid non-genomic actions of estradiol. Based on its ability to bind estradiol, GPR30 was renamed as G protein-coupled estrogen receptor (GPER). Unlike the other members of the GPCR family, which reside in the outer membrane of cells, GPER is localized in the endoplasmic reticulum.

GPER binds estradiol though not other endogenous estrogens, such as estrone or estriol, nor for other endogenous steroids, including progesterone, testosterone, and cortisol. Although potentially involved in signaling by aldosterone, GPER does not show any detectable binding towards aldosterone. Niacin and nicotinamide bind to the receptor in vitro with very low affinity. CCL18 has been identified as an endogenous antagonist of the GPER.

GPER is a member of the rhodopsin-like family of G protein-coupled receptors and is a multi-pass membrane protein that localizes to the endoplasmic reticulum. The protein binds estradiol, resulting in intracellular calcium mobilization and synthesis of phosphatidylinositol (3,4,5)-trisphosphate in the nucleus. This protein therefore plays a role in the rapid nongenomic signaling events widely observed following stimulation of cells and tissues with estradiol. The distribution of GPER is well established in the rodent, with high expression observed in the hypothalamus, pituitary gland, adrenal medulla, kidney medulla and developing follicles of the ovary GPER is expressed in the breasts, and activation by estradiol produces cell proliferation in both normal and malignant breast epithelial tissue. However, GPER knockout mice show no overt mammary phenotype, unlike ERα knockout mice, but similarly to ERβ knockout mice. This indicates that although GPER and ERβ play a modulatory role in breast development, ERα is the main receptor responsible for estrogen-mediated breast tissue growth. GPER is expressed in germ cells and has been found to be essential for male fertility, specifically, in spermatogenesis. GPER has been found to modulate gonadotropin-releasing hormone (GnRH) secretion in the hypothalamic-pituitary-gonadal (HPG) axis. GPER plays a role in breast cancer progression and tamoxifen resistance. GPER has also been proposed as a biomarker in triple-negative breast cancer.

GPER is expressed in the blood vessel endothelium and is responsible for vasodilation and as a result, blood pressure lowering effects of estrogen. GPER also regulates components of the renin-angiotensin system, which also controls blood pressure, and is required for superoxide-mediated cardiovascular function and aging.

GPER and ERα, but not ERβ, have been found to mediate the antidepressant-like effects of estradiol. Contrarily, activation of GPER has been found to be anxiogenic in mice, while activation of ERβ has been found to be anxiolytic. There is a high expression of GPER, as well as ERβ, in oxytocin neurons in various parts of the hypothalamus, including the paraventricular nucleus and the supraoptic nucleus. It is speculated that activation of GPER may be the mechanism by which estradiol mediates rapid effects on the oxytocin system, for instance, rapidly increasing oxytocin receptor expression. Estradiol has also been found to increase oxytocin levels and release in the medial preoptic area and medial basal hypothalamus, actions that may be mediated by activation of GPER and/or ERβ. Estradiol, as well as tamoxifen and fulvestrant, have been found to rapidly induce lordosis through activation of the GPER in female rats.

Female GPER knockout mice display hyperglycemia and impaired glucose tolerance, reduced body growth, and increased blood pressure. Male GPER knockout mice are observed to have increased growth, body fat, insulin resistance and glucose intolerance, dyslipidemia, increased osteoblast function (mineralization), resulting in higher bone mineral density and trabecular bone volume, and persistent growth plate activity resulting in longer bones.

III. COMPOUNDS AND SYNTHESIS

A. Compounds

The aralkyl-substituted aniline derivatives of the present disclosure are shown, for example, above, in the summary section and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

All of the aralkyl-substituted aniline derivatives of the present disclosure may be useful for the prevention and treatment of one or more diseases or disorders discussed herein. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all of the compounds of the present disclosure are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the aralkyl-substituted aniline derivatives of the present disclosure have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

The aralkyl-substituted aniline derivatives of the present disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration.

Chemical formulas used to represent aralkyl-substituted aniline derivatives of the present disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the aralkyl-substituted aniline derivatives of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The aralkyl-substituted aniline derivatives of the present disclosure may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

B. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "≡≡≡" represents a single bond or a double bond. Thus, the formula

covers, for example,

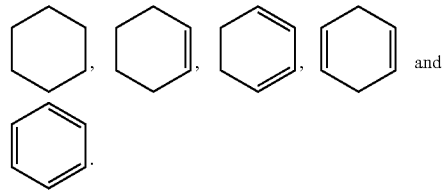

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⁓", when drawn perpendicularly across a bond (e.g.,

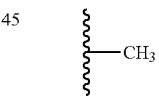

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⫼⫼⫼" means a single bond where the group attached to the thick end of the wedge is "into the page". The symbol "⁓" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

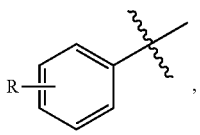

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

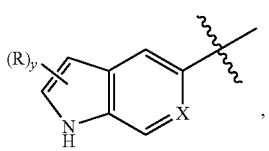

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom(s) in the moiety replacing a hydrogen atom is not counted. Thus methoxyhexyl, which has a total of seven carbon atoms, is an example of a substituted alkyl$_{(C1-6)}$.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to any non-aromatic ring present. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom on either the non-aromatic ring or an alkyl group attached thereto has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl, cycloalkyl, and/or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl and/or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

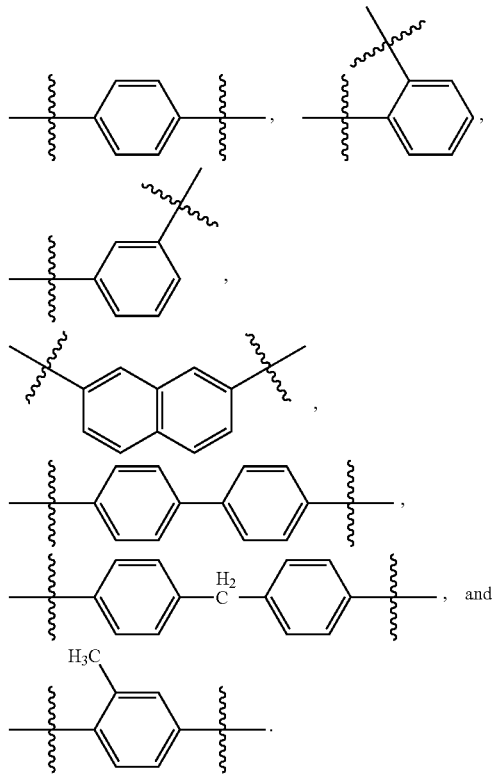

An "arene" refers to the class of compounds having the formula H—R, wherein R is aryl as that term is defined above. Benzene and toluene are non-limiting examples of arenes. When any of these terms are used with the "substituted" modifier one or more hydrogen atom on either the aromatic ring(s) or any alkyl, cycloalkyl, and/or aralkyl group attached thereto has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy" or "aryloxy", when used without the "substituted" modifier, refers to groups, defined as —OR, in which R is cycloalkyl or aryl, respectively. The term "alkylthio" when used without the "substituted" modifier refers to the group —SR, in which R is an alkyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

An "active ingredient" (AI) (also referred to as an active compound, active substance, active agent, pharmaceutical agent, agent, biologically active molecule, or a therapeutic compound) is the ingredient in a pharmaceutical drug or a pesticide that is biologically active. The similar terms active pharmaceutical ingredient (API) and bulk active are also used in medicine, and the term active substance may be used for pesticide formulations.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, horse, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug) is a drug used to diagnose, cure, treat, or prevent disease. An active ingredient (AI) (defined above) is the ingredient in a pharmaceutical drug or a pesticide that is biologically active. The similar terms active pharmaceutical ingredient (API) and bulk active are also used in medicine, and the term active substance may be used for pesticide formulations. Some medications and pesticide products may contain more than one active ingredient. In contrast with the active ingredients, the inactive ingredients are usually called excipients (defined above) in pharmaceutical contexts.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤35%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

IV. METHODS OF THERAPY

In some embodiments, the disclosure provides compositions and methods for the treatment of breast cancer. One of skill in the art will be aware of many treatments that may be combined with the methods of the present disclosure, some but not all of which are described below. In many contexts, it is not necessary that the tumor cell be killed or induced to undergo normal cell death or "apoptosis," although such may occur and be beneficial. Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

A. Formulations and Routes for Administration to Patients

In some embodiments, the disclosure provides a method of treating cancer comprising providing to a patient an effective amount of an agent according to the present disclosure. Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. This includes oral, nasal, buccal, rectal, vaginal or topical. Alternatively, administration may be by intradermal, subcutaneous, intramuscular, intraperitoneal or intravenous injection. Such compositions would normally be administered as pharmaceutically acceptable compositions. Of particular interest is direct intratumoral administration, perfusion of a tumor, or administration local or regional to a tumor, for example, in the local or regional vasculature or lymphatic system, or in a resected tumor bed (e.g., post-operative catheter). For practically any tumor, systemic delivery also is contemplated. This will prove especially important for attacking microscopic or metastatic cancer.

The active compounds may also be administered as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agent, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The actual dosage amount of a composition of the present disclosure administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

"Treatment" and "treating" refer to administration or application of a therapeutic agent to a subject or performance of a procedure or modality on a subject for the purpose of obtaining a therapeutic benefit of a disease or health-related condition.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease.

A "disease" can be any pathological condition of a body part, an organ, or a system resulting from any cause, such as infection, genetic defect, and/or environmental stress.

"Prevention" and "preventing" are used according to their ordinary and plain meaning to mean "acting before" or such an act. In the context of a particular disease, those terms refer to administration or application of an agent, drug, or remedy to a subject or performance of a procedure or modality on a subject for the purpose of blocking the onset of a disease or health-related condition.

The subject can be a subject who is known or suspected of being free of a particular disease or health-related condition at the time the relevant preventive agent is administered. The subject, for example, can be a subject with no known disease or health-related condition (i.e., a healthy subject).

In additional embodiments of the disclosure, methods include identifying a patient in need of treatment. A patient may be identified, for example, based on taking a patient history or based on findings on clinical examination.

B. Cancer Combination Treatments

In some embodiments, the method further comprises treating a patient with cancer with a conventional cancer treatment. One goal of current cancer research is to find ways to improve the efficacy of chemo- and radiotherapy, such as by combining traditional therapies with other anti-cancer treatments. In the context of the present disclosure, it is contemplated that this treatment could be, but is not limited to, chemotherapeutic, radiation, a polypeptide inducer of apoptosis or other therapeutic intervention. It also is conceivable that more than one administration of the treatment will be desired.

1. Chemotherapy

A wide variety of chemotherapeutic agents may be used in accordance with the present disclosure. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1; dynemicin, including dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein transferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and can be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of your internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

Another immunotherapy could also be used as part of a combined therapy with gen silencing therapy discussed above. In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8, CCL18 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds can be used to target the anti-cancer agents discussed herein.

Examples of immunotherapies currently under investigation or in use are immune adjuvants, e.g., *Mycobacterium bovis*, *Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used with the present disclosure. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon α, β, and γ; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present disclosure by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present disclosure to improve the anti-hyperproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

Yet other classes of compounds useful for combination therapy are PARP inhibitors. PARP inhibitors are a group of pharmacological inhibitors of the enzyme poly ADP ribose polymerase (PARP). They are developed for multiple indications; the most important is the treatment of cancer. Several forms of cancer are more dependent on PARP than regular cells, making PARP an attractive target for cancer therapy. In addition to their use in cancer therapy, PARP inhibitors are considered a potential treatment for acute life-threatening diseases, such as stroke and myocardial infarction, as well as for long-term neurodegenerative diseases.

DNA is damaged thousands of times during each cell cycle, and that damage must be repaired. BRCA1, BRCA2 and PALB2 are proteins that are important for the repair of double-strand DNA breaks by the error-free homologous recombinational repair, or HR, pathway. When the gene for either protein is mutated, the change can lead to errors in DNA repair that can eventually cause breast cancer. When subjected to enough damage at one time, the altered gene can cause the death of the cells. PARP1 is a protein that is important for repairing single-strand breaks ('nicks' in the DNA). If such nicks persist unrepaired until DNA is replicated (which must precede cell division), then the replication itself can cause double strand breaks to form.

Drugs that inhibit PARP1 cause multiple double strand breaks to form in this way, and in tumors with BRCA1, BRCA2 or PALB2 mutations these double strand breaks cannot be efficiently repaired, leading to the death of the cells. Normal cells that don't replicate their DNA as often as cancer cells, and that lack any mutated BRCA1 or BRCA2 still have homologous repair operating, which allows them to survive the inhibition of PARP. Some cancer cells that lack the tumor suppressor PTEN may be sensitive to PARP inhibitors because of downregulation of Rad51, a critical homologous recombination component, although other data suggest PTEN may not regulate Rad51. Hence PARP inhibitors may be effective against many PTEN-defective tumors. Cancer cells that are low in oxygen (e.g., in fast growing tumors) are sensitive to PARP inhibitors.

Researchers have recently discovered a significant new mechanism of action for three particular PARP inhibitors currently being tested in clinical trials. Prior to this study, PARP inhibitors were thought to work primarily by blocking PARP enzyme activity, thus preventing the repair of DNA damage and ultimately causing cell death. Now, scientists have established that PARP inhibitors have an additional role in localizing PARP proteins at sites of DNA damage, which has relevance to their anti-tumor activity. The trapped PARP protein-DNA complexes are highly toxic to cells because they block DNA replication. Under normal conditions, PARP1 and PARP2 are released from DNA once the repair process is underway. However, when they are bound to PARP inhibitors, PARP1 and PARP2 become trapped on DNA and are more toxic to cells than the unrepaired single-strand DNA breaks that accumulate in the absence of PARP activity, indicating that PARP inhibitors act as PARP poisons.

The main function of radiotherapy is to produce DNA strand breaks, causing severe DNA damage and leading to cell death. Radiotherapy has the potential to kill 100% of any targeted cells, but the dose required to do so would cause unacceptable side effects to healthy tissue. Radiotherapy therefore can only be given up to a certain level of radiation exposure. Combining radiation therapy with PARP inhibitors offers promise, since the inhibitors would lead to formation of double strand breaks from the single-strand breaks generated by the radiotherapy in tumor tissue with BRCA1/BRCA2 mutations. This combination could therefore lead to either more powerful therapy with the same radiation dose or similarly powerful therapy with a lower radiation dose.

Exemplary PARP inhibitors include Iniparib (BSI 201) for breast cancer and squamous cell lung cancer, Olaparib (AZD-2281) for breast, ovarian and colorectal cancer, Rucaparib (AG014699, PF-01367338) for metastatic breast and ovarian cancer, Veliparib (ABT-888) for metastatic melanoma and breast cancer, CEP 9722 for non-small-cell lung cancer (NSCLC), MK 4827, BMN-673 for advanced hematological malignancies and for advanced or recurrent solid tumors, and 3-aminobenzamide, a prototypical PARP inhibitor.

The cysteine protease, cathepsin L, is overexpressed in many cancer cell lines and in breast cancer tissue. It is a lysosomal proteolytic enzyme that is also transported into the cell nucleus where it acts on a few known substrates, including the N-terminal tail of histone H3, the transcription factor CDP/CUX, and as shown by the inventor, the Rb family of tumor suppressors and the DNA repair factor 53BP1. Most of the knowledge about the effect of cathepsin L in cancer relates to the secreted protein. Secreted cathepsin L is involved in the degradation of the extracellular matrix (ECM), the promotion of angiogenesis, and the recruitment and differentiation of stem cells. As a consequence, inhibition of cathepsin L holds great promise to delay tumour growth and metastasis. There is considerable interest in the enzyme as a target for synthesis and application of new potential anticancer agents. Recent progress has been made identifying a series of functionalized benzophenone, thiophene, pyridine, and fluorene thiosemicarbazone derivatives, which are potent inhibitors of cathepsin L with activity in the nanomolar range. In addition, selected compounds were found to inhibit the migration and invasion of prostate and breast cancer cells in preliminary experiments, as well as in a C3H mammary carcinoma system that models malignant breast tumour growth delay. In particular, a compound named KGP94 that inhibits specifically cathepsin L showed great promise in this mouse model. In addition, anti-angiogenic effects have been demonstrated with the cathepsin L inhibitor NSITC. This compound inhibited tumor growth in the CAM model of angiogenesis and in nude mouse xenograft models.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

E. Dosage

A compound according to the disclosure can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight In some embodiments, the effective dose range for the therapeutic compound can be extrapolated from effective doses determined in animal studies for a variety of different animals. In general a human equivalent dose (HED) in mg/kg can be calculated in accordance with the following formula (see, e.g., Reagan-Shaw et al., *FASEB J.*, 22(3):659-661, 2008, which is incorporated herein by reference):

$$\text{HED (mg/kg)} = \text{Animal dose (mg/kg)} \times (\text{Animal } K_m/\text{Human } K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

In one embodiment, the unit dose is administered once a day, e.g., or less frequently less than or at about every 2, 4, 8 or 30 days. In another embodiment, the unit dose is not administered with a frequency (e.g., not a regular frequency). For example, the unit dose may be administered a single time. Because the agent can persist for several days after administering, in many instances, it is possible to administer the composition with a frequency of less than once per day, or, for some instances, only once for the entire therapeutic regimen.

A compound featured in the disclosure can be administered in a single dose or in multiple doses. Where the administration of the compound is by infusion, the infusion can be a single sustained dose or can be delivered by multiple infusions. Injection of the compound can be directly into the tissue at or near the site of interest. Multiple injections of can be made into the tissue at or near the site.

In a particular dosage regimen, the compound is injected at or near a disease site once a day for seven days, for example, into a tumor, a tumor bed, or tumor vasculature. Where a dosage regimen comprises multiple administrations, it is understood that the effective amount of the compound administered to the subject can include the total amount of compound administered over the entire dosage regimen. One skilled in the art will appreciate that the exact individual dosages may be adjusted somewhat depending on a variety of factors, including the compound being administered, the time of administration, the route of administration, the nature of the formulation, the rate of excretion, the particular disorder being treated, the severity of the disorder, the pharmacodynamics of the compound, and the age, sex, weight, and general health of the patient. Wide variations in the necessary dosage level are to be expected in view of the differing efficiencies of the various routes of administration. Variations in these dosage levels can be adjusted using standard empirical routines of optimization, which are well-known in the art. The precise therapeutically effective dosage levels and patterns can be determined by the attending physician in consideration of the above-identified factors.

In one embodiment, a subject is administered an initial dose, and one or more maintenance doses of a compound. The maintenance dose or doses are generally lower than the initial dose, e.g., one-half less of the initial dose. The maintenance doses are generally administered no more than once every 5, 10, or 30 days. Further, the treatment regimen may last for a period of time which will vary depending upon the nature of the particular disease, its severity and the overall condition of the patient. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

Certain factors may influence the dosage required to effectively treat a subject, including but not limited to the severity of the disease or disorder, previous treatments, the general health and/or age of the subject, and other diseases present. It will also be appreciated that the effective dosage of the compound used for treatment may increase or decrease over the course of a particular treatment. Changes in dosage may result and become apparent from the results of diagnostic assays. For example, the subject can be monitored after administering a compound featured in this disclosure. Based on information from the monitoring, an additional amount of the compound can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on $EC_{50}$'s found to be effective in in vitro and in vivo animal models.

V. EXAMPLES

The following examples are included to demonstrate particular embodiments of the disclosure. It should be appreciated by those of skill in the art that the techniques disclosed in the examples which follow represent techniques discovered by the inventor to function well in the practice of the disclosure, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

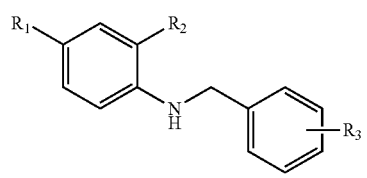

$R_1$ = isopropyl, methyl, tert-butyl
$R_2$ = cyclopropyl, cyclopentyl, cyclohexyl
$R_3$ = H, napthyl, biphenyl, 4-$CH_3$, 4-OMe, 4- Cl, 3,4-Cl

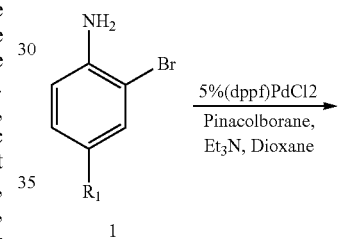

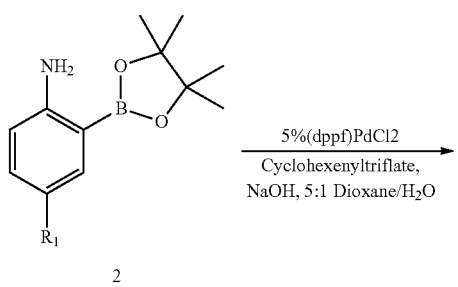

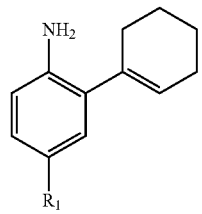

-continued

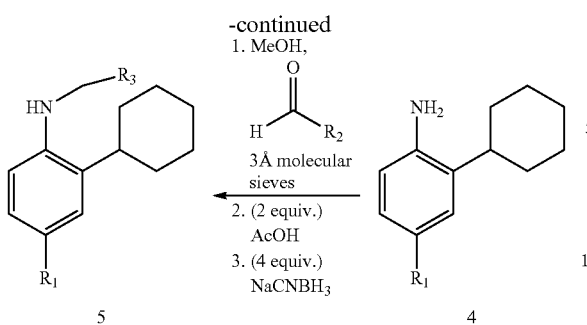

Substitution varied bromo-anilines were commercially purchased from Oakwood Chemical. A Miyuara borylation of the bromo-aniline and pinacolborane afforded a boronated aniline. Creating the boronate on the activated aniline, allowed for subsequent Suzuki coupling to a non-conjugated vinyl triflate. The olefin contained within the alkyl ring system could be removed with 10% palladium on carbon at 60 Psi and in methanol. Yields for this reaction were quantitative. Reductive amination of the primary amine and various aldehydes, afforded the products listed in Table 1. Yields for the reductive amination varied amongst all compounds with no general trend. All compounds were characterized and confirmed with $H^1$ and $C^{13}$ NMR.

Human Myelocytic Leukemia (HL-60) cells were grown in phenol red free media containing 10% activated fetal bovine serum (FBS), 1% Pen-Strep, and 1% Glutamax. Cells were grown to no more than $1 \times 10^6$ cells/mL to prevent differentiation before being split. Prior to assay cells were transferred to phenol red free media containing charcoal-stripped FBS. On the day of the assay cells were centrifuged down at 16.4 G for 5 minutes and washed with 50:1 HBSS/HEPES. Cells were resuspended at $1 \times 10^7$ cells/mL in 50:1 HBSS/HEPES. To the resuspended cells, 0.05% pluronic acid and 5 uM of fluorescent calcium indicator, Indo-1AM, were added. The dye solution was incubated for 0.5 hrs at room temperature with rocking. After 30 minutes cells were spun down, and resuspended in 50:1 HBSS/HEPES. Cells were placed on ice for at least 5 minutes and then resuspended in 8.5 mL of 50:1 HBSS/HEPES (containing probenacid) for agonism assays or 6.5 mL of 50:1 HBSS/HEPES (containing probenacid) for antagonism assays. For agonism assays 160 µL of cell suspension were added to a 96-well plate and were incubated at 37° for 10 minutes in a FlexStation® 3 plate reader (Molecular Devices). Inside the plate reader, 40 µL of agonist were added to each well and excited with 350 nm and read at emissions of 405 nm and 490 nm. For antagonist assays, 120 µL of cell suspension were added to a 96-well plate. In addition to the cell suspension 40 µL of antagonist were added to the wells. Cells with antagonists were incubated at 37° for 15 minutes in FlexStation® 3 plate reader (Molecular Devices). Inside the plate reader, 40 µL of agonist at the $EC_{80}$ were added to each well and excited with 350 nm and read at emissions of 405 nm and 490 nm.

Figure 2:
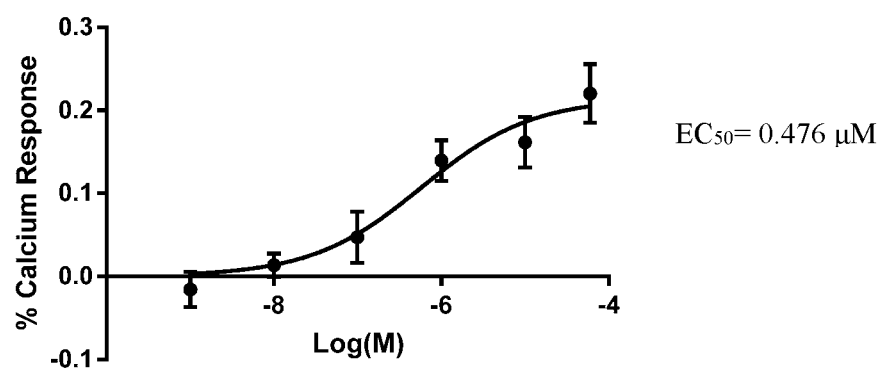
FIG. 2 shows agonism assays in which the $EC_{50}$ of 17β-Estradiol (E2) and known GPER agonist G-1 are determined.
Figure 3:
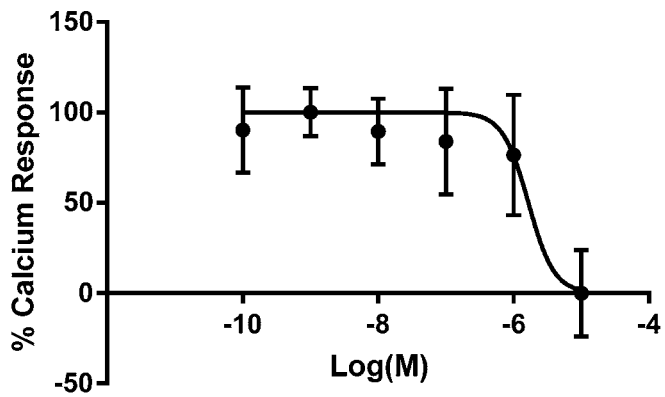
FIG. 3 shows antagonism assay in which the activity of known GPER agonist G-1 is attenuated with G-36 and G-15.
Figure 3:
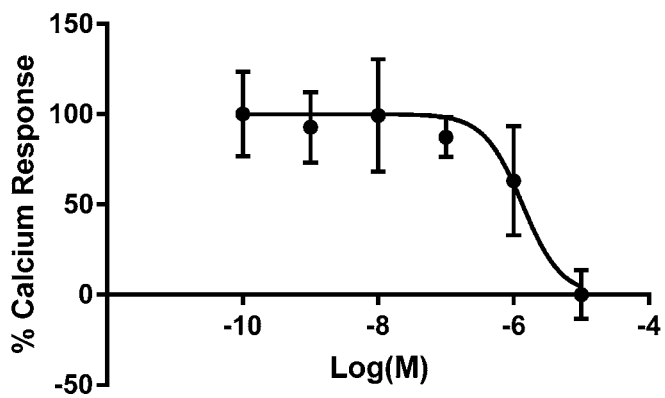

Evidence of GPER in the HL-60 cell line was established through treatment of HL-60 cells with varying concentrations of siRNA GPER (10 nM, 30 nM, and 50 nM) to signal the degradation of mRNA encoding for the expression of GPER. Treatment with anti-GPER antibody (Abcam) revealed the presence of a band located at 62 kDa as well as a decrease in the amount of GPER present with an increase in siRNA treatment (FIG. 1). While the predicted weight of GPER is expected to be a ~55 kDa, the apparent increase in the weight may be attributed to glycosylation. Once the presence of GPER was confirmed in the HL-60 cell line, the agonism of known agonists, 17β-Estradiol (E2) and G-1 (FIG. 2). This data was utilized to establish the $EC_{50}$ of the compounds within the assay. This $EC_{50}$ value and data were used to determine the $EC_{80}$ that would subsequently be used in the development of an antagonism assay. Before the compounds were tested for antagonism, the antagonism of G-1 with G-36 and G-15 was analyzed (FIG. 3).

Example 2—Results

The $IC_{50}$ values for G-36 and G-15 established a benchmark for the efficacy of antagonism for the compounds that were synthesized (Table 1).

TABLE 1

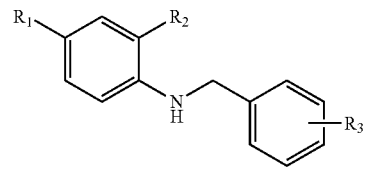

| Compound | $R_1$ | $R_2$ | $R_3$ | Red. Am. Yield |
|---|---|---|---|---|
| 1 | Isopropyl | Cyclohexyl | Napthyl | 61% |
| 2 | Isopropyl | Cyclohexyl | 4-Aryl | 77% |
| 3 | Isopropyl | Cyclohexyl | 4-CH$_3$ | 84% |
| 4 | Isopropyl | Cyclohexyl | 4-OMe | 31% |
| 5 | Isopropyl | Cyclohexyl | H | — |
| 6 | Isopropyl | Cyclohexyl | 4-Cl | 19% |
| 7 | Isopropyl | Cyclohexyl | 3,4-Cl | — |
| 8 | Methyl | Cyclohexyl | Napthyl | 71% |
| 9 | Methyl | Cyclohexyl | 4-Aryl | — |
| 10 | Methyl | Cyclohexyl | 4-CH$_3$ | 27% |
| 11 | Methyl | Cyclohexyl | 4-OMe | 18% |
| 12 | Methyl | Cyclohexyl | H | 74% |
| 13 | Methyl | Cyclohexyl | 4-Cl | 77% |
| 14 | Methyl | Cyclohexyl | 3,4-Cl | 89% |
| 15 | t-butyl | Cyclohexyl | Napthyl | 63% |
| 16 | t-butyl | Cyclohexyl | 4-Aryl | 94% |
| 17 | t-butyl | Cyclohexyl | 4-CH$_3$ | 87% |
| 18 | t-butyl | Cyclohexyl | 4-OMe | 93% |
| 19 | t-butyl | Cyclohexyl | H | — |
| 20 | t-butyl | Cyclohexyl | 4-Cl | 81% |
| 21 | t-butyl | Cyclohexyl | 3,4-Cl | 85% |

The antagonism protocol described above was utilized to determine the $IC_{50}$ values of the compounds (Table 2, ** indicates that data is based upon duplicate only; similar data in triplicate shown in Table 3, below). Compound 4 exhibits an $IC_{50}$ of 153 nM±6.05 nM and is thus the most active of the series in which the number of reproduction experiments is greater than two. Additional $IC_{50}$ data can be found in Table 2 (shown below).

TABLE 2

| Compound | $R_1$ | $R_3$ | $IC_{50}$ |
|---|---|---|---|
| 1 | Isopropyl | Napthyl | 313 nM ± 97.8 nM |
| 3 | Isopropyl | 4-CH$_3$ | 123 nM ± 24.4 nM |
| 4 | Isopropyl | 4-OMe | 155 nM ± 4.75 nM |
| 6 | Isopropyl | 4-Cl | 168 nM ± 16.1 nM |
| 7 | Isopropyl | 3,4-Cl | 319 nM ± 57.5 nM |
| 8 | Methyl | Napthyl | 349 nM ± 18.9 nM |
| 9 | Methyl | 4-Phenyl | 319 nM ± 3.6 nM |
| 10 | Methyl | 4-CH$_3$ | >10 uM |
| 11 | Methyl | 4-OMe | 940 nM ± 30.0 nM |
| 12 | Methyl | 4-H | >10 uM |

TABLE 2-continued

| Compound | $R_1$ | $R_3$ | $IC_{50}$ |
|---|---|---|---|
| 13 | Methyl | 4-Cl | 401 nM ± 234 nM |
| 14 | Methyl | 3,4-Cl | 2050 nM ± 776 nM |
| 15 | Tert-butyl | Napthyl | >10 uM |
| 16 | Tert-butyl | 4-Phenyl | 615 nM ± 30.1 nM |
| 17 | Tert-butyl | 4-$CH_3$ | 56.7 nM ± 20.9 nM |
| 18 | Tert-butyl | 4-OMe | 874 nM ± 49.5 nM |
| 19 | Tert-butyl | 4-H | 354 nM ± 195 nM |

** indicates that data is based upon a duplicate of triplicate readings.

Example 4—Experimental Methods

Chemistry. Compounds were synthesized according to the procedures listed in Supplemental SII. Characterization of compounds were performed utilizing NMR and high-resolution mass spectroscopy. H1 and C13 NMR spectra were performed in chloroform-D from Cambridge Isotope Laboratories (Andover, Mass.) on a 400 MHz Bruker AVANCE III. Data was analyzed utilizing TopSpin 3.2 software (Supplemental S III and S IV). High-resolution mass spectroscopy experimental work was carried out using a MaXis plus electrospray-quadrupole time-of-flight mass spectrometer (Bruker, Billerica, Mass.) (Supplemental S.IV). Ionization was by electrospray with the samples infused into the instrument in ~5 μM acetonitrile/water/formic acid (50/50/0.1%) solutions at a flow rate of 3 μl min$^{-1}$. Nitrogen was used as nebulizing, drying, and collision gas. HPLC-grade acetonitrile and water were purchased for Sigma-Aldrich (St. Louis, Mo.).

Cell Line and Culture. The human leukemia cell line (HL-60) used in this study were purchased from the American Type Culture Collection (Manassas, Va.). HL-60 cells were cultivated in RPMI 1640 media containing 10% (v/v) heat-inactivated fetal bovine serum (FBS), 1% (v/v) penicillin, and 1% (v/v) GlutaMax. Three days prior to assays HL-60 cells were switched the media containing 10% charcoal-stripped FBS. Cells were passaged every 3 days and maintained at a cell concentration below 1×10 (Kumar et al., 2004) to prevent differentiation. The cells were incubated at 37° C. under 5% $CO_2$.

In vitro biological evaluation using calcium mobilization. HL-60 cells were grown in 10% charcoal-stripped RPMI 72 hours before assays were performed. Cells were centrifuged and counted with a hemocytometer from Hausser Scientific (Bedford, Mass.). The assay required 100,000 cells per well, for a total number of cells on a 96-well plate assay of about 1×10 (Matthews and Gustafsson, 2003). HL-60 cells (1×10 (Matthews and Gustafsson, 2003)) were incubated in 50:1 Hanks balanced salt solution (Millipore Sigma, Saint Louis, Mo. and HEPES (Gibco by Life Technologies, Gaithersburg, Md.) containing 5 μM indo1-AM (Thermo Fischer Scientific, Waltham, Mass.) and 0.05% pluronic acid (AAT Bioquest Inc., Sunnyvale, Calif.) for 0.5 h at RT. Cells were spun down and washed with 50:1 HBSS/HEPES, and resuspended in media. Resuspension was placed on ice for no longer than 5 mins. Cells were loaded into plate at 100,000 cells/well. For agonist cells were immediately incubated for 15 mins at 37° C. Following the 15 mins incubation FlexStation 3 Multimode Plate Reader (Molecular Devices, Sunnyvale, Calif.) added the appropriate amount of agonist and was read for 150 seconds at 37° C. For antagonists once the cells were seeded, antagonist was added and incubated for 15 mins at 37° C. After 15 mins of equilibration, the $EC_{80}$ of G-1 was added by the FlexStation and read for 150 secs at 37° C. Calcium mobilization was determined ratiometrically using $\lambda_{ex}$ 350 nm and $\lambda_{em}$ 405/490 nm.

In vitro cAMP biological evaluation. A homogeneous time resolved fluorescence (HTRF®) components for cAMP was purchased by CisBio (Bedford, Mass.). HL-60 cells were grown in 10% charcoal-stripped RPMI media for 72 hours prior to assays. Cells were centrifuged and counted with a hemocytometer from Hausser Scientific (Horsham, Pa.). The total number of cells needed to complete the assay was determined based upon 8,000 cells/well. The determined number of cells was diluted in 5:1 (5×) stimulation buffer contain 500 μM of 3-isobutyl-1-methylxanthine (IBMX) (Sigma Aldrich, Saint Louis, Mo.). To an HTRF 96-well low volume white plate from CisBio, 5 μL of cold cell suspension was added to each plate, followed by 4 μL of (2.5×) of agonist or stimulation buffer (negative control and non-stimulated cells). Cells were covered with a clear plastic film and incubated at 37° C. for 15 mins in an incubator. After 15 mins cell 1 μL of 10 μM (10×) forskolin was added to each well. The plate was once again sealed and incubated at 37° C. for 15 mins. After 15 mins 5 μL of cAMP-$d_2$ (acceptor) was added to all wells, including controls. Conversely, 5 μL of monoclonal anti-cAMP Eu3$^+$ cryptate (donor) was added to only the wells with test compound and non-stimulated cells. Following addition, the plate was sealed, covered with aluminum foil, and incubated at room temperature for 30 mins. After the allotted time cells were read using Flexstation3 and with $\lambda_{ex}$ 314 nm and $\lambda_{em}$ 665 nm. For an antagonism platform the procedure was slightly altered. The $EC_{80}$ of G-1 was recalculated based upon cAMP agonism results. To the plate, 2 μL of (5×) antagonist were added dose wise followed by the addition of 5 μL of cold cell suspension to all wells (top and bottom well were designated as G-1 control and forskolin control, respectively). Cells and antagonists were incubated for 15 mins at 37° C. After 15 mins, 2 μL of the (5×) $EC_{80}$ of G-1 was added to wells with antagonist. For the G-1 control, 2 μL of 5:1 stimulation buffer and 2 uL of the (5×) $EC_{80}$ G-1 were added. For the forskolin control, 4 μL of 5:1 stimulation buffer and 1 μL of (10×) forskolin were combined. For all other wells, following the addition of antagonists, cells, and agonists 1 μL of (10×) forskolin were add for a final concentration of 1 μM. After the addition of forskolin, cells were incubated at 37° C. for 5 minutes before dyes and lysis buffer were added as described previously. Cells were allowed to equilibrate at room temperature for 30 minutes before being read at $\lambda_{ex}$ 314 nm and $\lambda_{em}$ 665 nm.

ERα and ERβ Fluorescence Polarization Assay. The ERα and ERβ PolarScreen™ Competitor Assays by Invitrogen (Carlsbad, Calif.) were purchased. The concentrations of the ERα and ERβ enzyme varied between the two assays. A 4× sample of ERα was prepared for a final concentration of 75 nM. Conversely, a 4× sample of ERβ was prepared for a final concentration of 23 nM within the assay. For both ERα and ERβ a 4× aliquot of Fluoromone was prepared for a final assay concentration of 4.5 nM. Despite the differences in concentration of ERα and ERβ, the binding assay protocol for the two different enzymes remained the same. Drug dilutions were prepared for a 2× dilution in the ER specific buffer that was provided within the assay kit. In addition to the drug dilutions a 2× aliquot of Fluoromone was prepared by adding 10 μL of 4× with 10 μL of ER specific buffer. A 2× dilution of enzyme and fluorophore was achieved by adding equal portions of each to each other. To a black 384-plate well plate, 10 μL of compound were added to the wells followed by 10 μL of the 2× mixture of enzyme and fluoromone. Two controls were included in the plate design.

In one control, enzyme and compound were omitted so that only ER specific buffer and fluoromone remained. A separate control contained the enzyme and fluoromone control. Once all components were added the plate was covered with a film and aluminum foil. The plate was incubated at RT for 2 hours before being read with $\lambda_{ex}$ 485 nm and $\lambda_{em}$ 535 nm.

Animal and diet. Although inbred AKR/J mice have been found to be a gallstone-resistant strain, they are still susceptible to the formation of E2-induced cholesterol gallstones (Wang et al., 2004). Mice were maintained in a temperature-controlled room (22±1° C.) with a 12-hour day cycle (lights on 0600 h-1800 h) and were provided free access to water and normal mouse chow containing trace cholesterol (<0.02%) (Lab Rodent Diet, St. Louis, Mo.). To exclude possible interindividual differences in endogenous estrogen concentrations, all female mice, at the age of 4 weeks, were ovariectomized (OVX). At 8 weeks of age, these mice were implanted subcutaneously with pellets (Innovative Research of America, Sarasota, Fla.) releasing 17β-estradiol (E2) at 6 µg/day for 8 weeks. To explore the effect of the GPR30 selective antagonist SG-1 on cholesterol gallstone formation, the mice, at 8 weeks old, were injected intramuscularly with SG-1 at 0, 0.016, or 0.032 mg/day/kg, as well as fed the lithogenic diet containing 1% cholesterol, 15% butter fat, and 0.5% cholic acid for 8 weeks. All procedures were in accordance with current NIH guidelines and were approved by the Institutional Animal Care and Use Committees of Albert Einstein College of Medicine (Bronx, N.Y.) and Saint Louis University (St. Louis, Mo.).

Gallstone studies. After 8 weeks of feeding the lithogenic diet, mice were fasted overnight but had free access to water. After anesthetization with pentobarbital, a cholecystectomy was performed during laparotomy. The entire gallbladder bile was studied by polarized light microscopy without a cover slip and then with a cover slip using phase contrast optics for observing the presence of mucin gel, liquid crystals, cholesterol monohydrate crystals, sandy stones, and real gallstones according to previously established criteria (Wang et al., 1997). The images of cholesterol monohydrate crystals and gallstones were analyzed by a Carl Zeiss Imaging System with an AxioVision Rel 4.6 software (Carl Zeiss Microimaging GmbH, Göttingen, Germany). After microscopic analysis, gallbladder bile was collected, frozen and stored at −20° C. for lipid studies.

Biliary lipid analysis. Cholesterol, phospholipid and bile salt concentrations in pooled gallbladder bile were determined according to previously published methods (Wang et al., 2016). Cholesterol saturation index (CSI) of pooled gallbladder bile was calculated from critical tables (Wang et al., 2016) that was established for taurocholate, the predominant bile salts in bile of mice on the lithogenic diet (Wang et al., 1999). Relative lipid compositions of pooled gallbladder bile were plotted on condensed phased diagrams. For graphic analysis, the phase limits of the micellar zones and the crystallization pathways were extrapolated from model systems developed for taurocholate at 37° C. and at a total lipid concentration of ~10 g/dL (Wang and Carey, 1996).

Liver accumulation study. After liver samples were collected from mouse gallstone experiments, they were immediately frozen and stored at −80° C. until analysis. Tissue samples were weighed and placed into Eppendorf tubes. Corresponding naïve tissues were used to prepare standard curves in a tissue matrix. To each sample or standard tissue, the appropriate volume of cold PBS was added to achieve a tissue concentration of 200 mg/mL. Stainless steel beads (2-3 mm) were added the tubes that were then placed in a bead beater for 1-2 minutes. Tissue samples and standards (100 µL) were then added to a 96-well plate. Standards (100 µL) were added to a separate 96-well plate. To each tissue well, 400 uL of cold acetonitrile containing 100 ng/mL internal standard enalapril was added. Plates were vortexed for 5 minutes at 4° C., then centrifuged at 3200 rpm at 4° C. for 10 minutes. The supernatant (400 µL) was transferred to a second 96-well plate, evaporated to dryness under nitrogen, reconstituted with 100 µL of 0.1% v/v formic acid in 9:1 water:acetonitrile, and vortexed for 5 minutes, briefly centrifuged, and submitted for LC/MS analysis. Compound concentrations were determined on a Sciex API-4000 LC/MS system in positive electrospray mode. Analytes were eluted from an Amour C18 reverse phase column (2.1×30 mm, 5 µm) using a 0.1% formic acid (aqueous) to 100% acetonitrile gradient mobile phase system at a flow rate of 0.35 mL/min. Peak areas for the specific mass transitions were integrated using Analyst 1.5.1 software. Peak area ratios of analyte to internal standard were plotted against concentration with a 1/x-weighted linear regression to determine compound concentration.

Statistics. The 50% excitatory ($EC_{50}$) and 50% inhibitory concentrations ($IC_{50}$) were determined by nonlinear regression analysis using GraphPad Prism, version 5.02 (GraphPad Inc, La Jolla, Calif.). All ANOVA analyses were also run using GraphPad Prism, version 5.02. A P value<0.05 was considered as significant.

Example 5—Results

Design and synthesis of GPER antagonists. The inventors' previous docking studies pointed to the possible importance of hydrogen bonding to N310 (Matthews and Gustafsson, 2003 and Arnatt et al., 2013) (Ballesteros-Weinstein numbering) and E275 (Kumar et al., 2004 and Baell and Holloway, 2010), π-π stacking with F208 (extracellular loop 2, EL2) and H307 (Matthews and Gustafsson, 2003 and Everhart, 2004), and various hydrophobic interactions with an extensive hydrophobic pocket (Arnatt et al., 2013). From this work, a scaffold was designed following the proposed pharmacophore, FIG. 2 (Arnatt and Zhang, 2012). The proposed scaffold consists of two benzene rings connected via a secondary amine linker. One of these benzene rings is intended to interact with F208 (EL2) and H307 (Matthews and Gustafsson, 2003 and Everhart, 2004) and the other is meant to hold two hydrophobic moieties, $R_1$ and $R_2$, to interact with the hydrophobic pocket. The secondary amine linker is anticipated to hydrogen bond to N310 (Matthews and Gustafsson, 2003 and Arnatt et al., 2013), and varying substituents at $R_3$ have been included to explore the binding pocket in that region.

The synthetic route of the GPER antagonists is summarized in FIG. 3. All brominated anilines (isopropyl, methyl, and t-butyl) were available commercially, therefore, they served as a logical starting point for the synthesis. The brominated anilines underwent Pd-catalyzed Miyaura Borylation with pinacolborane to produce borylated anilines (2a, 2b, 2c). The reaction of 1-cyclohexenyl trifluoromethansulfonate successfully coupled to the borylated anilines to form 3a, 3b, and 3c. Catalytic hydrogenation of the coupled cyclohexenyl ring was afforded quantitatively in 10% Pd/C and $H_2$ to give 4a, 4b, and 4c. The final step of the synthetic route involved the reductive amination between the prepared aniline (4a, 4b, and 4C) and various aldehydes ($R_2$) to yield 5-25. The aldehydes were chosen to study variation in size and electrostatic properties that may be favorable within the binding pocket of GPER.

Figure 4:
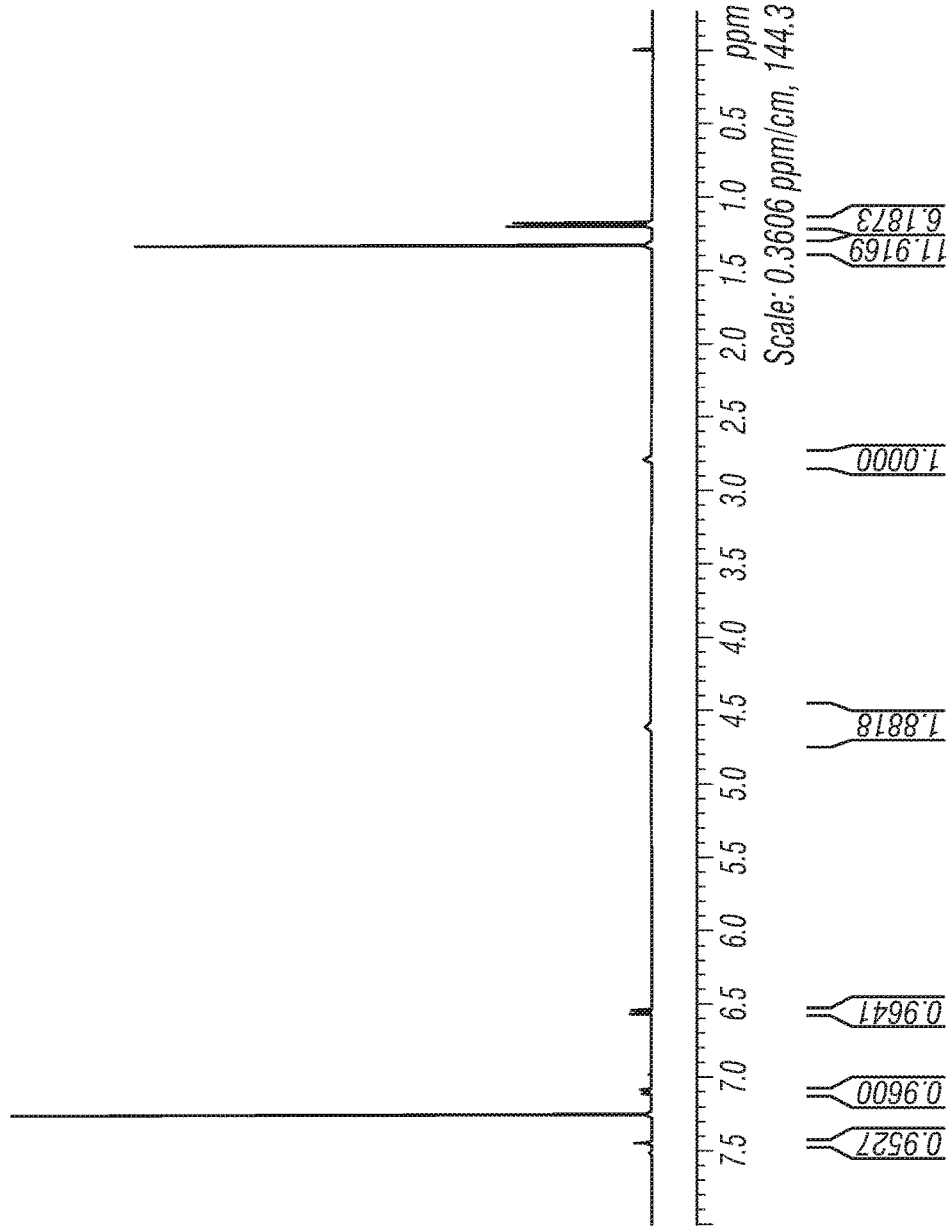
FIG. 4 Example $H^1$ NMR showing the product resulting from the Miyuara Borylation FIG. 5 Example $H^1$ NMR showing the product resulting from the Suzuki Coupling FIG. 6. Example $H^1$ NMR showing the product resulting from the hydrogenation of an olefin using 10% Pd/C at 60 Psi.

E2 is a partial agonist of GPER. While developing functional assays used in this study, the inventors noticed functional differences between the GPER agonists E2 and G-1. Due to the difference in structures and receptor selectivity, these results were not surprising. Both calcium mobilization and cAMP assays were run using HL-60 cells (a human promyelocytic leukemia cell line) which endogenously expresses GPER (FIG. 4) (Blesson and Sahlin, 2012). For calcium mobilization, the $EC_{50}$ value for G-1 was 1.71±0.07 µM and the $EC_{50}$ value for E2 was 0.629±0.15 µM. The % $E_{max}$ of E2 was 48.1±3.2% when compared to the maximum of G-1 calcium response (P≤0.001). This is the first evidence of partial agonism of GPER. The inventors observed the same trend in $EC_{50}$ values for $G_{i/o}$ mediated cAMP inhibition: the $EC_{50}$ value for G-1 was 766±38 nM and the $EC_{50}$ value for E2 was 190±41 nM. However, for cAMP inhibition, they did not observe a statistically significant (P>0.05) difference between the $E_{max}$ values for G-1 and E2. This effect may be assay dependent due to the addition of forskolin or a cell line dependent due to the endogenous expression of ERα and ERβ in HL-60 cells (Blesson and Sahlin, 2012 and Hill et al., 2010). Overall, since G-1 is a full agonist and is selective for GPER, the inventors chose to use its $EC_{80}$ concentration in the inventors' antagonism assays (Bologa et al., 2006).

Inhibition of calcium mobilization by GPER antagonists 5-25. Prior to running antagonism assays, compounds 5-25 were tested for GPER agonism in a similar fashion as G-1, and no compounds showed agonism below 10 µM. Within the antagonism assay, almost every compound had an $IC_{50}$ value in the high nanomolar range (Table 3). In the calcium mobilization assay, the determined $IC_{50}$ values of G-15 and G-36 were determined to be 1550±170 nM and 1350±220 nM, respectively. The previously published $IC_{50}$ values of G-15 and G-36 were reported to be 185 nM and 165 nM, respectively (Dennis et al., 2011). The variation in the reported and the observed $IC_{50}$ values for G-15 and G-36 may exist due to differences in antagonism assay methodology. In the study that reported $IC_{50}$ values for calcium mobilization, 200 nM of G-1 was chosen as the concentration to antagonize against because at that concentration there was a similar amount of calcium mobilization in SKBr3 cells for both E2 and G-1 (Dennis et al., 2011). However, the standard method for performing an antagonism assay requires the $EC_{80/90}$ value of the agonist to create the necessary signal window for detecting inhibitory response (Liu et al., 2010, Lee et al., 2014, Noblin et al., 2012 and Arkin et al., 2012). In all, the experimentally determined $IC_{50}$ values presented in this study vary by approximately a 10-fold magnitude to the $IC_{50}$ values reported in the literature. This observed difference is approximately the same fold magnitude between the different values of G-1 (200 nM in previous study (Dennis et al., 2011) vs. 3 µM in this study) used to agonize the cells in the separate studies.

In this series of compounds (5-25) the $R_1$ substitution greatly impacted GPER antagonism. Larger hydrophobic groups (isopropyl and tert-butyl) were well tolerated at $R_1$, whereas the methyl substituted compounds (12-18) generally exhibited the lowest antagonism activity. For the $R_1$ substitution, isopropyl derivatives (5-11) generally had lower $IC_{50}$ values than the tert-butyl derivatives (19-25). Overall, this suggests that there is a limit to the size that the GPER binding pocket can tolerate in that position. The changes in activity caused by the $R_2$ substitutions are less clear-cut. While mono-substitution is favored over 3-4-disubstitution (11, 18, and 25), there are insufficient compounds to verify if 3- or 4-position is favored. The larger $R_2$ substituents such as napthyl or biphenyl (5, 6, 12, 13, 19, and 20) generally had mixed tolerances based upon the $R_1$ substitution. These differences may have arisen due to the size of the GPER binding pocket or the existence of different binding modes for those compounds. The 4-Cl derivatives (10, 17, and 24) were unaffected by the $R_1$ substitution, whereas the other small substituents were all affected by the R1 substitution. The two compounds with the lowest $IC_{50}$ values, 8 ($R_1$=isopropyl, $R_2$=4-OMe) and 21 ($R_1$=tert-butyl, $R_2$=4-$CH_3$), have different substitution patterns and illustrate the potential for further optimization through future SAR studies.

Figure 5:
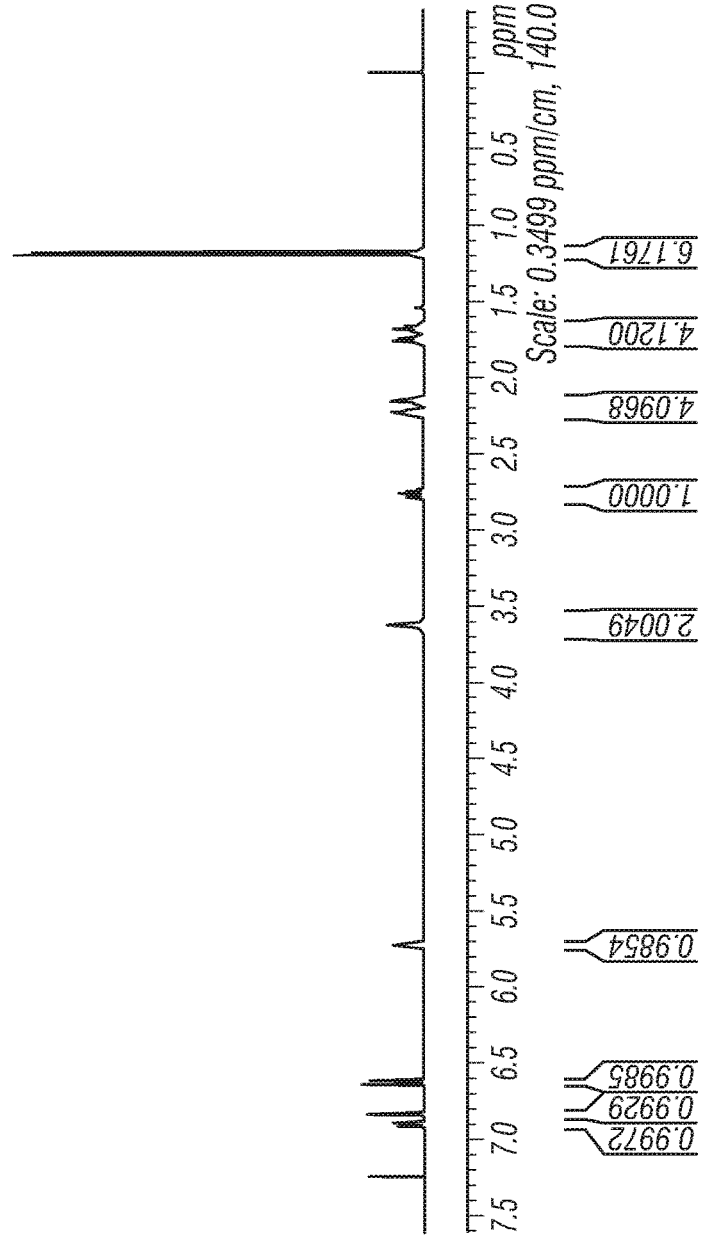

Antagonism of $G_{i/o}$ activity and selectivity of 8 and 21. Current evidence indicates that GPER promiscuously couples to both $G_{i/o}$ and $G_s$ and that this effect is cell line and tissue specific (Filardo et al., 2000 and Filardo et al., 2002). Within the HL-60 cell line, the majority of G-proteins have been found to be pertussis toxin sensitive $G_i$-proteins despite the expression of both $G_s$- and $G_q$-proteins (Klinker et al., 1996). These results agree with this previously published observation, as the inventors were able to achieve signaling exclusively through the $G_{i/o}$ pathway but not the $G_s$ pathway for selective GPER agonist, G-1. Compounds 8 and 21 were compared to a known GPER antagonist, G-36, and all three compounds could antagonize G-1 induced inhibition of adenylate cyclase (FIG. 5). At 1 µM exposure, all three compounds caused a decrease in adenylate cyclase inhibition. This effect was also observed, less so, at 100 nM for the compounds, with both 8 and 21 having slightly higher efficacy than G-36.

Since estrogenic compounds can bind to ERα, ERβ, and GPER, the selectivity for 8 and 21 for GPER over the classical estrogen receptors was established. Unlike E2, for ERα there was no appreciable binding observed for G-1, G-36, or 8 at any tested concentration (data not shown). At the highest concentration (10 µM), 21 showed a low level of binding that was significantly different than G-1, G-36, and 8 at the same concentration. Since binding was exhibited at high concentrations, 21 may be limited in effectiveness as a GPER antagonist due to potential off target effects. Studies of ERβ binding revealed that at high concentrations (10 µM) only G-1 and G-36 exhibited binding to ERβ (data not shown). Conversely, both 8 and 21 at the same 10 µM concentration showed a lack of binding. Overall, both 8 and 21 do not exhibit binding to either ERα or ERβ below 10 µM; however, 8 displayed greater selectivity since no binding was exhibited at higher concentrations. Compound 8 will be referred to henceforth as SG-1 (Saint Louis University GPER compound 1).

Figure 6:
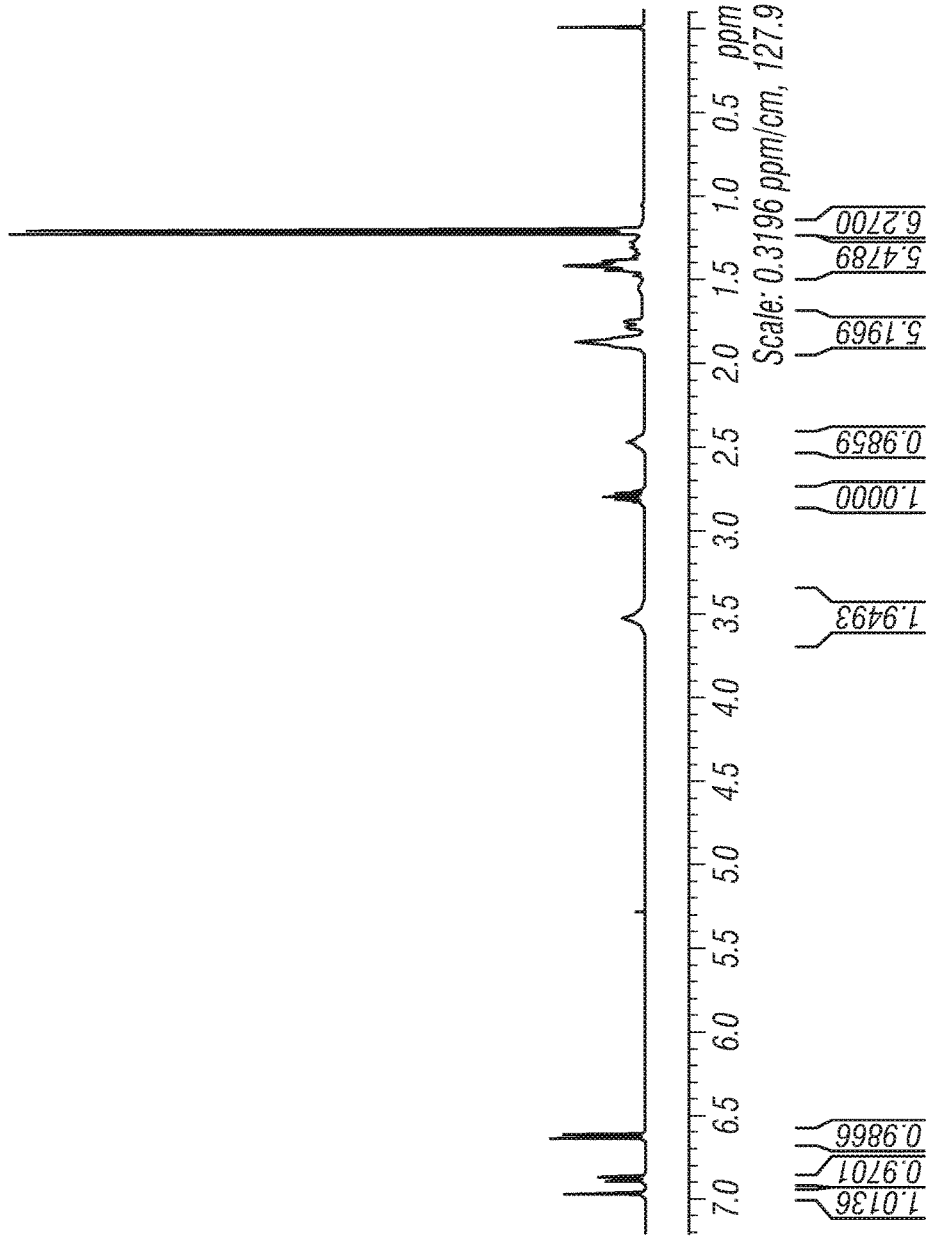
Figure 7:
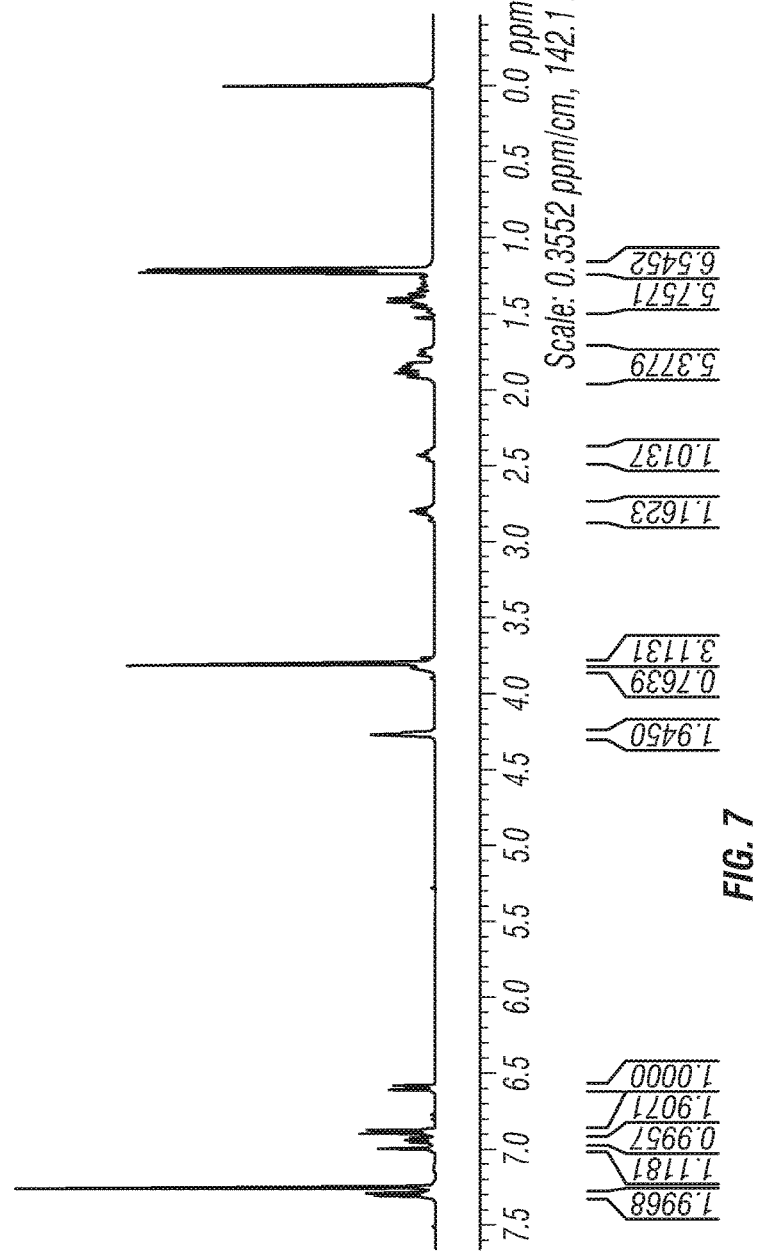
FIG. 7. $H^1$ NMR SG-1 (also referred to as Compound 4) resulting from the reductive amination.
Figure 8:
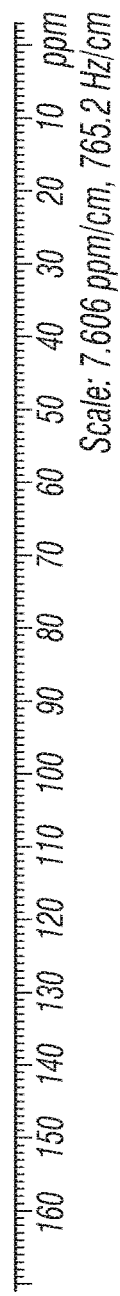
FIG. 8. $C^{13}$ NMR SG-1 resulting from the reductive amination.
Figure 9:
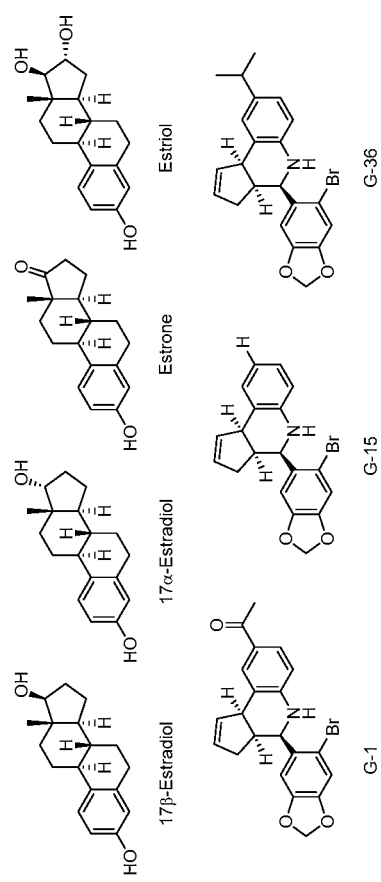
FIG. 9. Structure of compounds and synthetic, GPER-specific compounds known to bind to GPER.
Figure 10:
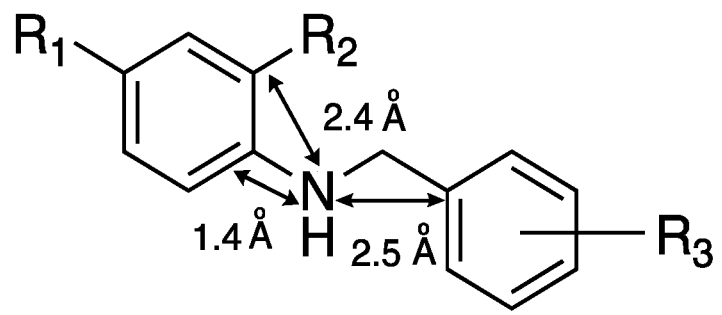
FIG. 10. Scaffold used in the design of GPER antagonists.
Figure 11:
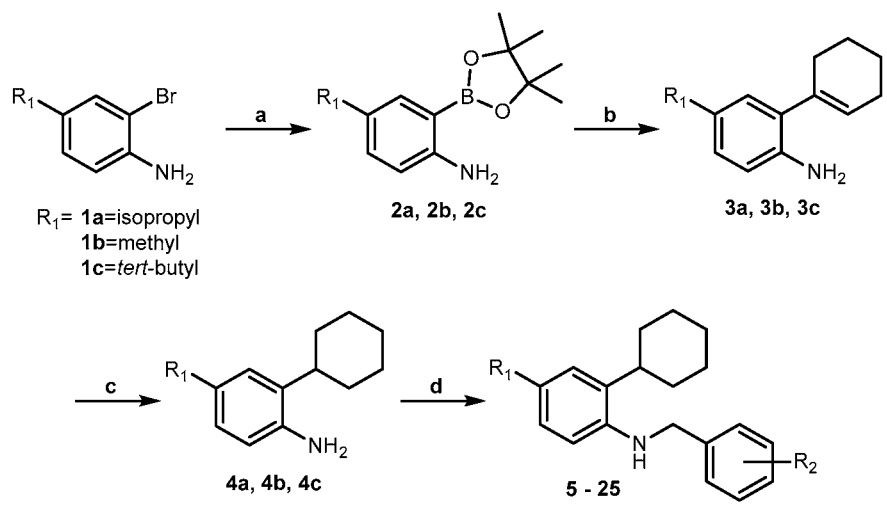
FIG. 11. (a) 5 mol % (dppf)PdCl$_2$, Et$_3$N, Pinacolborane, Dioxane, 90-100° C., 18 h; (b) 5 mol % (dppf)PdCl$_2$, NaOH, 1-cyclohexenyl trifluoromethanesulfonate, 5:1 dioxane/H$_2$O, 90-100° C., 24 h; (c) 10% Pd/C, 60 Psi H$_2$, 1.5 h; (d) R$_2$-aldehyde, AcOH (2 equiv.), 1.5 A m.s., NaCNBH$_3$ (6 equiv.), RT; R$_2$=2-napthaldehyde, biphenyl-4-carboxaldehyde, p-tolualdehyde, p-anisaldehyde, benzaldehyde, 3-chlorobenzaldehyde, and 3,4-chlorobenzaldehyde.
Figure 12:
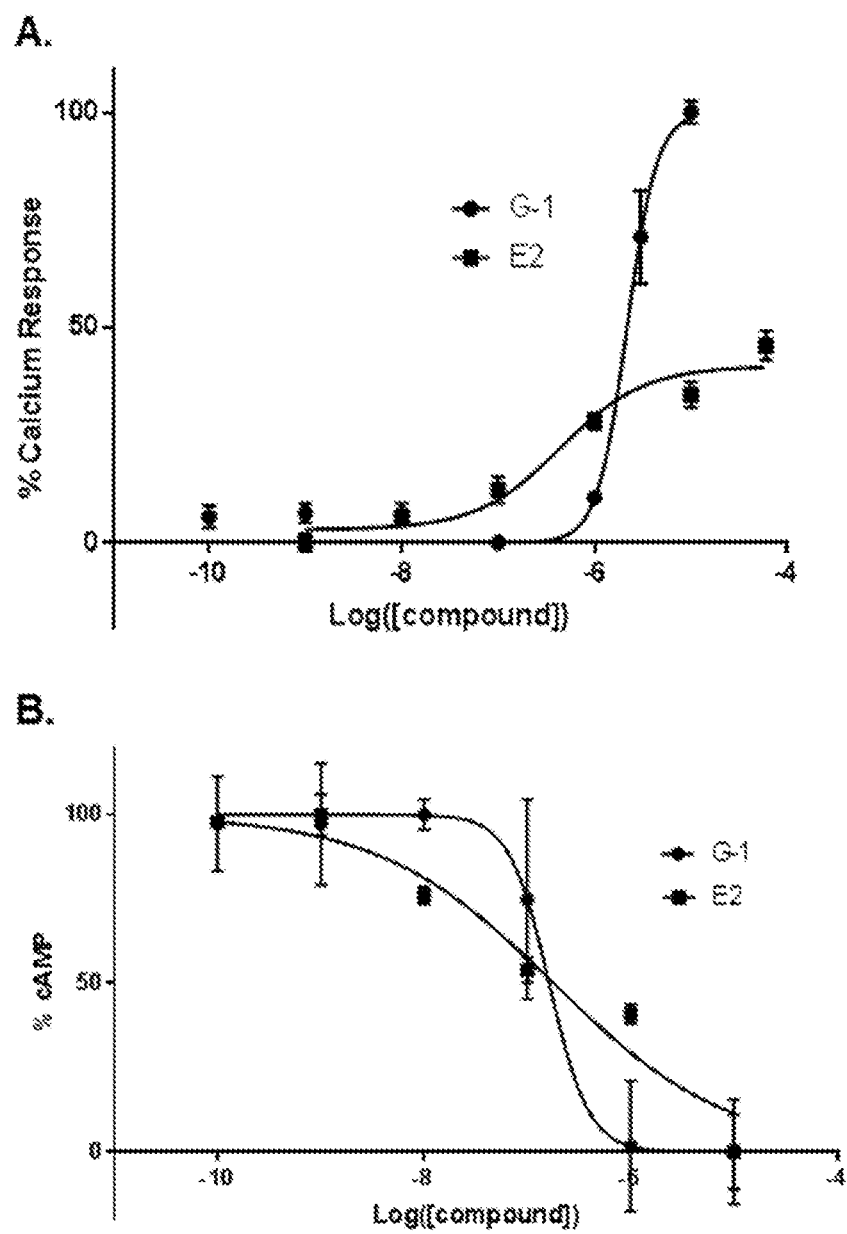
FIG. 12. Comparison in signaling of G-1 and E2 (A) Differences in calcium mobilization of selective GPER agonist, G-1, and E2 agonism were evaluated using indo1-AM-loaded HL-60 cells. G-1 exhibited an $EC_{50}$ value of 1.71±0.07 μM whereas E2 displayed an $EC_{50}$ value of 0.629±0.15 μM, which is approximately half the response of G-1. (B) Disparity in agonism of G-1 and E2 was also evident in cAMP evaluation. G-1 displayed an $EC_{50}$ value of 766±38 nM, which was greater than $EC_{50}$ value of E2 (190±41 nM). Each dose curve was run as a n=3 and is representative of 3 separate assays.

Prevalence of estrogen-induced gallstones in mice is significantly reduced by SG-1. To further understand the role that GPER plays in estrogen-induced gallstones, SG-1 was studied in ovariectomized (OVX) AKR/J (gallstone resistant) mice that exposed to a lithogenic (high fat/cholesterol) diet and exogenous E2. FIG. 6A shows that 100% of E2-treated OVX mice develop gallstones. However, gallstone prevalence is significantly reduced to 40% in E2-treated OVX mice receiving SG-1 at 0.032 mg/day/kg for 8 weeks. SG-1 treatment at 0.016 mg/day/kg slightly decreased gallstone prevalence to 80% in E2-treated OVX mice. FIG. 6B displays representative photomicrographs of amorphous mucin gel, liquid crystals, cholesterol monohydrate crystals, and gallstones as observed by polarizing light microscopy in these mice. As shown in Table 4, E2-treated OVX mice exhibit the highest mole percent cholesterol and CSI value in pooled gallbladder bile. In contrast, mole percent cholesterol in gallbladder bile was gradually reduced with an increase in doses of SG-1. Thus, CSI values of pooled gallbladder bile were dramatically decreased from 1.61 to 1.23 by SG-1 (Table 4), which is consistent with a dose-dependent reduction in gallstone prevalence in E2-treated OVX mice receiving various doses of SG-1 (FIG. 6A). FIG. 6C shows that the relative lipid composition of pooled gallbladder bile from E2-treated OVX mice fed the lithogenic diet for 8 weeks is located in the central three-phase area denoted Region C on a taurocholate-rich bile phase diagram, in where the bile is composed of solid cholesterol monohydrate crystals, liquid crystals, and saturated micelles (Wang and Carey, 1996). With an increase in doses of SG-1, the relative lipid composition of pooled gallbladder bile progressively shifted downward and to the left of the phase diagram. These alterations were caused by a dramatic reduction in cholesterol content, a relative decrease in phospholipid content, and a relative increase in bile salt content (Table 4). Utilizing pooled liver tissue taken from the mice used in the above study and HPLC/MS, the inventors also determined that SG-1 was adsorbed into the liver at both dosages. At 0.016 mg/day/kg, they found 1 ng/mL of SG-1 in the liver, and at 0.032 mg/day/kg they found 5 ng/mL of SG-1. In all, these results are consistent with a dose-dependent reduction in gallstone prevalence in E2-treated OVX mice receiving SG-1 from 0 to 0.032 mg/day/kg (FIG. 6A).

FIG. 6D exhibits the effect of E2 and SG-1 on expression of GPER, ERα and ERβ in the liver. Compared to control mice receiving neither E2 nor SG-1, expression of GPER was significantly increased. However, expression of GPER was significantly reduced by SG-1 in a dose-dependent manner. Of note, expression of ERα is significantly increased in three groups of mice treated with E2, regardless of whether mice received varying doses of SG-1. As expected, expression of ERβ is slightly increased in all mice because its expression is approximately 50-fold lower compared to ERα in the mouse liver (Wang et al., 2004).

TABLE 3

$IC_{50}$ values of the inhibition of calcium mobilization in HL-60 cells endogenously expressing GPER

| | $R_1$ | $R_2$ | $IC_{50}$ (nM) |
|---|---|---|---|
| G-15 | — | — | 1550 ± 170 |
| G-36 | — | — | 1350 ± 220 |
| 5 | Isopropyl | Napthyl | 260 ± 110 |
| 6 | Isopropyl | 4-Phenyl | 191 ± 74 |
| 7 | Isopropyl | 4-CH$_3$ | 131 ± 21 |
| 8[#] | Isopropyl | 4-OMe | 75.0 ± 13.7 |
| 9 | Isopropyl | 4-H | >10,000 |
| 10 | Isopropyl | 4-Cl | 197 ± 43 |
| 11 | Isopropyl | 3,4-Cl | 255 ± 102 |
| 12 | Methyl | Napthyl | 338 ± 22 |
| 13 | Methyl | 4-Phenyl | 365 ± 65 |

TABLE 3-continued $IC_{50}$ values of the inhibition of calcium mobilization in HL-60 cells endogenously expressing GPER

| | $R_1$ | $R_2$ | $IC_{50}$ (nM) |
|---|---|---|---|
| 14 | Methyl | 4-CH$_3$ | >10,000 |
| 15 | Methyl | 4-OMe | 949 ± 28 |
| 16 | Methyl | 4-H | >10,000 |
| 17 | Methyl | 4-Cl | 167 ± 17 |
| 18 | Methyl | 3,4-Cl | 2050 ± 780 |
| 19 | Tert-butyl | Napthyl | >10,000 |
| 20 | Tert-butyl | 4-Phenyl | 132 ± 145 |
| 21 | Tert-butyl | 4-CH$_3$ | 60.8 ± 18.0 |
| 22 | Tert-butyl | 4-OMe | 874 ± 49 |
| 23 | Tert-butyl | 4-H | 331 ± 160 |
| 24 | Tert-butyl | 4-Cl | 141 ± 14 |
| 25 | Tert-butyl | 3,4-Cl | 657 ± 94 |

G-15 and G-36 are displayed as a standard benchmark for GPER antagonism that can be used to compare 5-25. The $IC_{50}$ values are expressed as means ± the standard deviations. Each $IC_{50}$ value is an average of three separate $IC_{50}$ values obtained from triplicate measurements and the standard deviation is calculated from those three separate $IC_{50}$ values.
[#]This compound is later referred to as SG-1.

TABLE 4

Biliary lipid compositions of gallbladder bile

| 17β-Estradiol (μg/day) | SG-1 (mg/day/kg) | Cholesterol (Mole %) | Phospholipids (Mole %) | Bile Salts (Mole %) | Cholesterol Phospholipids Ratio | Cholesterol Bile Salts Ratio | Total Lipid Concentration (g/dL) | CSI |
|---|---|---|---|---|---|---|---|---|
| 6 | 0 | 10.19 | 17.69 | 72.12 | 0.58 | 0.14 | 9.82 | 1.61 |
| 6 | 0.016 | 8.89 | 16.90 | 74.22 | 0.53 | 0.12 | 9.70 | 1.46 |
| 6 | 0.032 | 7.00 | 15.46 | 77.54 | 0.45 | 0.09 | 10.01 | 1.23 |

Values were determined from pooled gallbladder bile (n = 10 per group).

Example 6—Discussion

The implication of GPER in a diverse range of conditions and disease has necessitated the demand for new compounds. While the G-series (G-1, G-15, and G-36) has become the standard for GPER agonists and antagonists, these compounds have limited solubility. Additionally, the G-series compounds possess a tetrahydroquinoline structure, which is often a pan assay interference (PAIN) that can appear frequently as a hit in high throughput screens (HTS). The non-selective nature of the tetrahydroquinoline may limit the effectiveness of the compounds due to potential promicuous protein binding (Baell and Holloway, 2010). Building off previous molecular modeling studies and pharmacophore design, the inventors rationally and successfully created a new series of GPER antagonists and developed the first ever structure-activity-relationship for GPER (Arnatt et al., 2013 and Arnatt and Zhang, 2012).

Based upon the proposed scaffold, the inventors were able to develop a simplistic synthetic route and synthesized the initial set of compounds (5-25) with varying substituents. Results from the calcium mobilization assay show that almost every one of these compounds was an antagonist of GPER. Remarkably, during the development of the first high-throughput functional assay for GPER, the inventors discovered that E2 is a partial agonist of GPER when compared to G-1 (% $E_{max}$=48.1±3.2%). The exact mechanism for this partial agonism of GPER is unknown, but it may help explain the difficult pharmacology of GPER and its varying tissue-specific responses (Prossnitz and Arterburn, 2015 and Langer et al., 2010).

From the series of compounds, the inventors have developed a preliminary structure-activity-relationship for this scaffold. Since the overall size of the molecule play a key role in the activity, the inventors can begin to deduce that GPER has a defined binding pocket, which the inventors can begin to explore. Molecular modeling studies from the inventors' group and others are in agreement that in silico estrogenic compounds all bind within a similar binding pocket as each other (Arnatt et al., 2013, Arnatt and Zhang, 2012, Mendez-Luna et al., 2015, Rosano et al., 2016, Moreno-Ulloa, 2015, Vidad et al., 2016, Lappano et al., 2015 and Chimento et al., 2014). Among the series of compounds, SG-1 (8) and 21 displayed superior antagonism of G-1 signaling activity in the HL-60 cell line. These two molecules have different substitutions at both the $R_1$ and $R_2$ position of the scaffold, SG-1 ($R_1$=isopropyl, $R_2$=4-OMe) and 21 ($R_1$=tert-butyl, $R_2$=4-CH$_3$). Overall, at the $R_1$ substitution, GPER prefers bulkier hydrophobic groups, but varying the bulkiness of that groups influences what is tolerated at the $R_2$ substitution. At the $R_2$ position, smaller electron donating groups are favored when $R_1$ is either an isopropyl or tert-butyl group. The electron donating nature of these two groups are most likely making an electron rich aromatic ring, which is influencing either aryl-aryl or arylcation interactions (Bissantz et al., 2010). Overall, the data provided by these results has provided key insights into the structure-activity relationship that can be utilized in the development of new compound that can modulate GPER activity.

Validation of calcium mobilization data was performed by evaluating cAMP through the $G_{i/o}$ pathway. G-36, SG-1, and 21 were able to decrease inhibition of adenylate cyclase induced by G-1. Selectivity of SG-1 and 21 for GPER over ERα or ERβ was verified. While SG-1 did not bind to either estrogen receptor, 21 displayed binding to ERβ at 10 µM. Due to the proposed similarity between the binding pockets for the three estrogen receptors, it is not surprising to observe some binding (Bologa et al., 2006, Dennis et al., 2009 and Dennis et al., 2011).

Current evidence shows that women are twice as likely to develop cholesterol gallstones as men, and that oral contraceptives or other estrogenic therapies significantly increase that risk (Cirillo et al., 2005). While the classical estrogen receptor, ERα, plays a key role in estrogen's lithogenic effects, emerging evidence has shown that GPER is also involved in estrogen-dependent lithogenic pathways (de Bari et al., 2015 and Zucchetti et al., 2014). In an in vivo model of estrogen-induced gallstone formation, SG-1 is capable of reducing gallstone formation in a dose-dependent manner. At the highest concentration, 0.032 mg/day/kg, SG-1 does not completely inhibit the formation of cholesterol gallstones in OVX mice. One explanation for this observation is that higher dosages of SG-1 are needed to fully inhibit gallstone formation. However, the most likely explanation is that since SG-1 does not bind to other estrogen receptors, ERα is still being activated by E2 and inducing a basal level of gallstones (de Bari et al., 2015). In all, the discovery of SG-1 now opens the possibility for a new treatment of gallstones other than surgery or oral litholysis. Furthermore, SG-1 and the other compounds from this study offer new pharmacological tools to evaluate the function of GPER and explore its ligand binding domain.

All of the methods and compounds disclosed and claimed herein can be made and executed without undue experimentation in light of the present disclosure. While the compositions and methods of this disclosure have been described in terms of particular embodiments, it will be apparent to those of skill in the art that variations may be applied to the methods and apparatus and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference.

U.S. Pat. No. 5,739,169
U.S. Pat. No. 5,801,005
U.S. Pat. No. 5,824,311
U.S. Pat. No. 5,830,880
U.S. Pat. No. 5,846,945
Arkin et al., S. FLIPR Assays for GPCR and Ion Channel Targets. World-wide-web at ncbi.nlm.nih.gov/books/NBK92012/.
Arnatt et al., In *Computational Approaches to Nuclear Receptors*, The Royal Society of Chemistry: pp 117-137, 2012.
Arnatt et al., *Molecular Informatics*, 32 (7), 647-658, 2013.
Austin-Ward and Villaseca, *Revista Medica de Chile*, 126 (7):838-845, 1998.
Baell and Holloway, *Journal of Medicinal Chemistry*, 53 (7), 2719-2740, 2010.
Bissantz et al., *Journal of Medicinal Chemistry*, 53 (14), 5061-5084, 2010.
Blesson and Sahlin, *Molecular and Cellular Endocrinology*, 361 (1), 179-190, 2012.
Bologa et al., *Nature chemical biology*, 2 (4), 207-12, 2006.
Bukowski et al., *Clinical Cancer Res.*, 4(10):2337-2347, 1998.
Carey et al., *Journal of lipid research*, 19 (8), 945-55, 1978.
Chimento et al., *Molecular Nutrition & Food Research*, 58 (3), 478-489, 2014.
Christodoulides et al., *Microbiology*, 144(Pt 11):3027-3037, 1998.
Cirillo et al., *JAMA: the journal of the American Medical Association*, 293 (3), 330-9, 2005.
Davidson et al., *J. Immunother.*, 21(5):389-398, 1998.
de Bari et al., *J Lipid Res*, 56 (9), 1691-700, 2015.
Dennis et al., *J Steroid Biochem Mol Biol*, 127 (3-5), 358-66, 2011.
Dennis et al., *Nature chemical biology*, 5 (6), 421-7, 2009.
Everhart, In *The burden of digestive diseases in the United States. US Department of Health and Human Services, Public Health Service, National Institutes of Health, National Institute of Diabetes and Digestive and Kidney Diseases*, Everhart, J., Ed. US Government Printing Office: Washington, D.C., pp NIH Publication No. 09-6443 pp 115-117, 137-147, 2004.
Filardo et al., *Mol Endocrinol*, 14 (10), 1649-60, 2000.
Filardo et al., *Mol Endocrinol*, 16 (1), 70-84, 2002.

Hanibuchi et al., *Int. J. Cancer*, 78(4):480-485, 1998.
Hellstrand et al., *Acta Oncologica*, 37(4):347-353, 1998.
Hill et al., *Br J Pharmacol*, 161 (6), 1266-75, 2010.
Hui and Hashimoto, *Infection Immun.*, 66(11):5329-5336, 1998.
Klinker et al., *General Pharmacology: The Vascular System*, 27 (1), 33-54, 1996.
Kumar et al., *Essays In Biochemistry*, 40, 27, 2004.
Langer et al., *Steroids*, 75 (8), 603-610, 2010.
Lappano et al., *Current cancer drug targets*, 12 (5), 531-42, 2012.
Lappano et al., *Dis Model Mech*, 8 (10), 1237-46, 2015.
Lee et al., *Assay and Drug Development Technologies*, 12 (6), 361-368, 2014.
Liu et al., *Yi chuan=Hereditas/Zhongguo yi chuan xue hui bian ji*, 32 (3), 254-63, 2010.
Matthews & Gustafsson, *Mol Interv*, 3 (4), 281-92, 2003.
Mendez-Luna et al., *Journal of biomolecular structure & dynamics*, 33 (10), 2161-72, 2015.
Moreno-Ulloa et al., *Pharmacological Research*, 100 (Supplement C), 309-320, 2015.
Noblin et al., *Assay and Drug Development Technologies*, 10 (5), 457-467, 2012.
Pietras et al., *Oncogene*, 17(17):2235-2249, 1998.
Qin et al., *Proc. Natl. Acad. Sci. USA*, 95(24):14411-14416, 1998.
Rosano et al., *Aaps j*, 18 (1), 41-6, 2016.
Vidad et al., *bioRxiv* 2016.
Wang et al., *Gastroenterology*, 127 (1), 239-49, 2004.
Wang et al., *Hepatology*, 64 (3), 853-64, 2016.
Wang et al., *J Lipid Res*, 38 (7), 1395-411, 1997.
Wang et al., *Journal of lipid research*, 37 (3), 606-30, 1996.
Wang et al., *The American journal of physiology*, 276 (3 Pt 1), G751-60, 1999.
Zucchetti et al., *Hepatology*, 59 (3), 1016-1029, 2014.

What is claimed is:

1. A compound of the formula:

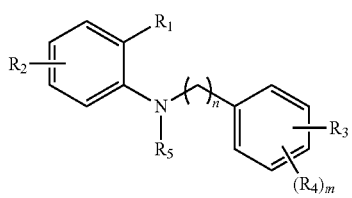

(I)

wherein:
R$_1$ is cycloalkyl$_{(C\leq 12)}$ substituted cycloalkyl$_{(C\leq 12)}$;
R$_2$ is alkyl$_{(C\leq 12)}$, cycloalkyl$_{(C\leq 12)}$, aryl$_{(C\leq 12)}$, or a substituted version of any of these groups;
R$_3$ and R$_4$ are each independently hydrogen, amino, halo, or hydroxy, or alkyl$_{(C\leq 12)}$, cycloalkyl$_{(C\leq 12)}$, aryl$_{(C\leq 12)}$, alkoxy$_{(C\leq 12)}$, or a substituted version of any of these groups; or
R$_3$ and R$_4$ are taken together and are alkenediyl$_{(C\leq 8)}$ and form a second aromatic ring;
R$_5$ is hydrogen, alkyl$_{(C\leq 6)}$, or substituted alkyl$_{(C\leq 6)}$;
m is 0, 1, 2, or 3; and
n is 1 or 2;
or a pharmaceutically acceptable salt thereof.

2. The compound of claim 1 further defined as:

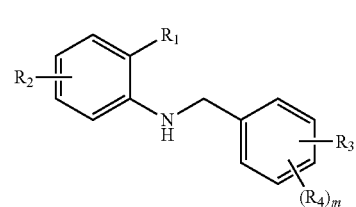

(II)

wherein:
R$_1$ is cycloalkyl$_{(C\leq 12)}$ substituted cycloalkyl$_{(C\leq 12)}$;
R$_2$ is alkyl$_{(C\leq 12)}$, cycloalkyl$_{(C\leq 12)}$, aryl$_{(C\leq 12)}$, or a substituted version of any of these groups;
R$_3$ and R$_4$ are each independently hydrogen, amino, halo, or hydroxy, or alkyl$_{(C\leq 12)}$, cycloalkyl$_{(C\leq 12)}$, aryl$_{(C\leq 12)}$, alkoxy$_{(C\leq 12)}$, or a substituted version of any of these groups; or
R$_3$ and R$_4$ are taken together and are alkenediyl$_{(C\leq 8)}$ and form a second aromatic ring; and
m is 0, 1, 2, or 3;
or a pharmaceutically acceptable salt thereof.

3. The compound of claim 1 further defined as:

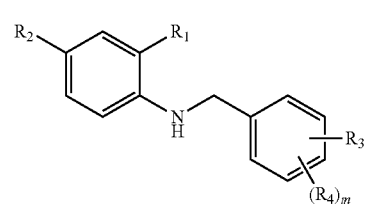

(III)

wherein R$_1$, R$_2$, R$_3$, R$_4$, and m are as defined above;
or a pharmaceutically acceptable salt thereof.

4. The compound according to claim 1, wherein R$_1$ is cycloalkyl$_{(C\leq 8)}$.

5. The compound according to claim 1, wherein R$_2$ is alkyl$_{(C\leq 6)}$ or substituted alkyl$_{(C\leq 6)}$.

6. The compound according to claim 1, wherein R$_3$ is alkyl$_{(C\leq 6)}$.

7. The compound according to claim 1, wherein R$_3$ is alkoxy$_{(C\leq 6)}$.

8. The compound according to claim 1, wherein R$_3$ is aryl$_{(C\leq 8)}$.

9. The compound according to claim 1, wherein R$_3$ is halo.

10. The compound according to claim 1, wherein R$_3$ is hydrogen.

11. The compound according to claim 1, wherein R$_3$ and R$_4$ are taken together and form a second fused phenyl ring.

12. The compound according to claim 1, wherein R$_4$ is halo.

13. The compound according to claim 1, wherein R$_5$ is hydrogen.

14. The compound according to claim 1, wherein n is 1.

15. The compound according to claim 1, wherein m is 0 or 1.

16. The compound according to claim 1, wherein the compound is further defined as:

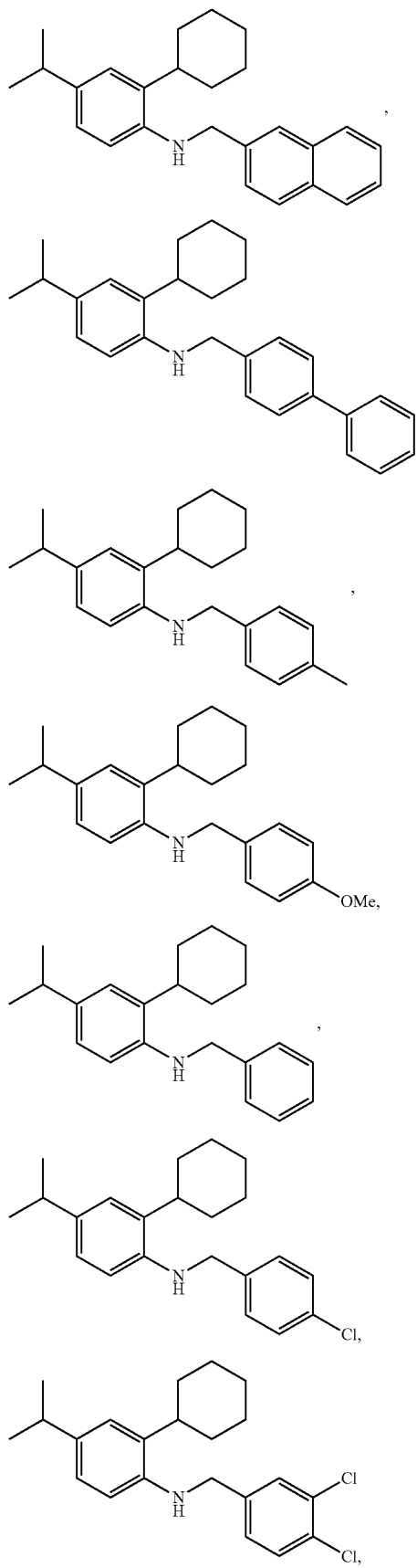
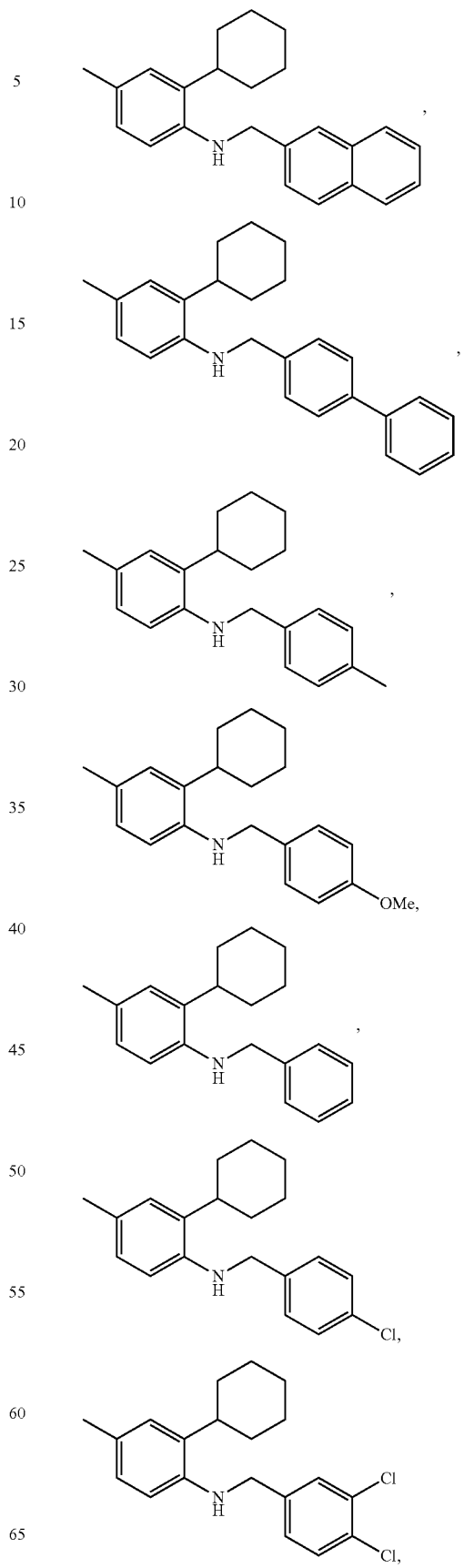

-continued

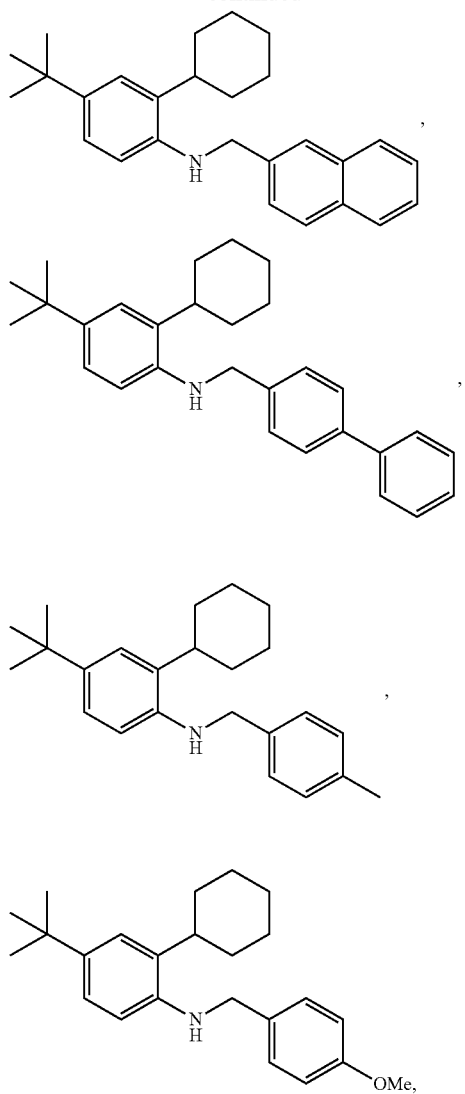

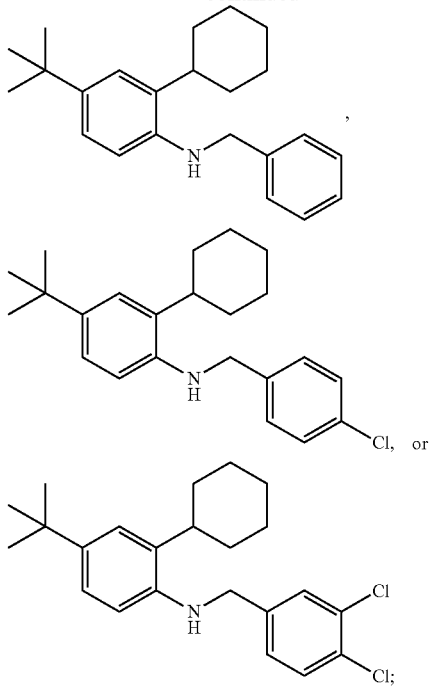

or a pharmaceutically acceptable salt thereof.

17. A pharmaceutical composition comprising:
(A) a compound according to claim 1; and
(B) an excipient.

18. A method of treating a disease or disorder in, or providing for neuroprotection of, a patient in need thereof comprising administering to the patient a therapeutically effective amount of a compound or pharmaceutical composition according to claim 1.

19. The method of claim 18, wherein the disease or disorder is cancer or gallstone disease.

20. A method of modulating the activity of a G protein-coupled estrogen receptor (GPER) comprising contacting the GPER with a compound or a pharmaceutical composition according to claim 1.

UNITED STATES PATENT AND TRADEMARK OFFICE
CERTIFICATE OF CORRECTION

PATENT NO. : 11,634,378 B2
APPLICATION NO. : 16/498571
DATED : April 25, 2023
INVENTOR(S) : Christopher Kent Arnatt It is certified that error appears in the above-identified patent and that said Letters Patent is hereby corrected as shown below:

In the Claims

Column 59, Claim 1, Line 54, "$R_1$ is cycloalkyl$_{(C£12)}$ substituted cycloalkyl$_{(C£12)}$;" should read --$R_1$ is cycloalkyl$_{(C\leq12)}$ substituted cycloalkyl$_{(C\leq12)}$;--,
 Line 55, "$R_2$ is alkyl$_{(C£12)}$, cycloalkyl$_{(C£12)}$, aryl$_{(C£12)}$, or a sub-" should read --$R_2$ is alkyl$_{(C\leq12)}$, cycloalkyl$_{(C\leq12)}$, aryl$_{(C\leq12)}$, or a sub- --,
 Line 58, "halo, or hydroxy, or alkyl$_{(C£12)}$, cycloalkyl$_{(C£12)}$," should read --halo, or hydroxy, or alkyl$_{(C\leq12)}$, cycloalkyl$_{(C\leq12)}$,--,
 Line 59, "aryl$_{(C£12)}$, alkoxy$_{(C£12)}$, or a substituted version of" should read --aryl$_{(C\leq12)}$, alkoxy$_{(C\leq12)}$, or a substituted version of--,
 Line 61, "$R_3$ and $R_4$ are taken together and are alkenediyl$_{(C£8)}$" should read --$R_3$ and $R_4$ are taken together and are alkenediyl$_{(C\leq8)}$--,
 Line 63, "$R_5$ is hydrogen, alkyl$_{(C£6)}$, or substituted alkyl$_{(C£6)}$;" should read --$R_5$ is hydrogen, alkyl$_{(C\leq6)}$, or substituted alkyl$_{(C\leq6)}$;--.

Column 60, Claim 2, Line 14, "$R_1$ is cycloalkyl$_{(C£12)}$ substituted cycloalkyl$_{(C£12)}$;" should read --$R_1$ is cycloalkyl$_{(C\leq12)}$ substituted cycloalkyl$_{(C\leq12)}$;--,
 Line 15, "$R_2$ is alkyl$_{(C£12)}$, cycloalkyl$_{(C£12)}$, aryl$_{(C£12)}$, or a sub-" should read --$R_2$ is alkyl$_{(C\leq12)}$, cycloalkyl$_{(C\leq12)}$, aryl$_{(C\leq12)}$, or a sub- --,
 Line 18, "halo, or hydroxy, or alkyl$_{(C£12)}$, cycloalkyl$_{(C£12)}$," should read --halo, or hydroxy, or alkyl$_{(C\leq12)}$, cycloalkyl$_{(C\leq12)}$,--,
 Line 19, "aryl$_{(C£12)}$, alkoxy$_{(C£12)}$, or a substituted version of" should read --aryl$_{(C\leq12)}$, alkoxy$_{(C\leq12)}$, or a substituted version of--,
 Line 21, "$R_3$ and $R_4$ are taken together and are alkenediyl$_{(C£8)}$" should read --$R_3$ and $R_4$ are taken together and are alkenediyl$_{(C\leq8)}$--.

Column 60, Claim 4, Line 42, "cycloalkyl$_{(C£8)}$." should read --cycloalkyl$_{(C\leq8)}$.--.

Column 60, Claim 5, Line 44, "alkyl$_{(C£6)}$ or substituted alkyl$_{(C£6)}$." should read --alkyl$_{(C\leq6)}$ or substituted alkyl$_{(C\leq6)}$.--.

Signed and Sealed this
Thirtieth Day of May, 2023

*Katherine Kelly Vidal*

Katherine Kelly Vidal
*Director of the United States Patent and Trademark Office*

Column 60, Claim 6, Line 46, "alkyl$_{(C≤6)}$." should read --alkyl$_{(C≤6)}$.--.

Column 60, Claim 7, Line 58, "alkoxy$_{(C≤6)}$." should read --alkoxy$_{(C≤6)}$.--.

Column 60, Claim 8, Line 52, "aryl$_{(C≤8)}$." should read --aryl$_{(C≤8)}$.--.